United States Patent
Welch et al.

(10) Patent No.: US 10,487,121 B2
(45) Date of Patent: Nov. 26, 2019

(54) D-PEPTIDE INHIBITORS OF HIV ENTRY AND METHODS OF USE

(71) Applicants: Navigen, Inc., Salt Lake City, UT (US); UNIVERSITY OF UTAH RESEARCH FOUNDATION, Salt Lake City, UT (US)

(72) Inventors: Brett D. Welch, Salt Lake City, UT (US); James Nicholas Francis, Salt Lake City, UT (US); Michael S. Kay, Salt Lake City, UT (US)

(73) Assignees: Navigen, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/068,306

(22) PCT Filed: Jan. 6, 2017

(86) PCT No.: PCT/US2017/012640
§ 371 (c)(1),
(2) Date: Jul. 5, 2018

(87) PCT Pub. No.: WO2017/120549
PCT Pub. Date: Jul. 13, 2017

(65) Prior Publication Data
US 2019/0023748 A1    Jan. 24, 2019

Related U.S. Application Data

(60) Provisional application No. 62/276,201, filed on Jan. 7, 2016, provisional application No. 62/372,257, filed on Aug. 8, 2016.

(51) Int. Cl.
*C07K 14/16* (2006.01)
*A61K 38/08* (2019.01)
(Continued)

(52) U.S. Cl.
CPC ............ *C07K 14/162* (2013.01); *A61K 38/08* (2013.01); *A61K 38/10* (2013.01); *A61K 47/542* (2017.08);
(Continued)

(58) Field of Classification Search
CPC .... A61K 38/162; A61K 48/00; A61K 47/641; A61K 38/02; A61K 47/42; C12N 2760/14133; G01N 2333/162
See application file for complete search history.

(56) References Cited

U.S. PATENT DOCUMENTS 6,506,554 B1   1/2003  Chan et al.
6,818,740 B1   11/2004  Eckert et al.
(Continued)

FOREIGN PATENT DOCUMENTS

WO   2005/018666 A1   3/2005
WO   2005/080418 A2   9/2005
(Continued)

OTHER PUBLICATIONS

Bianchi et al., "Covalent stabilization of coiled coils of the HIV gp41 N region yields extremely potent and broad inhibitors of viral infection," *Proceedings of the National Academy of Sciences of the United States of America* 102(36):12903-12908, 2005.
(Continued)

*Primary Examiner* — Marcela M Cordero Garcia
*Assistant Examiner* — Jia-Hai Lee
(74) *Attorney, Agent, or Firm* — Seed IP Law Group LLC

(57) ABSTRACT

Disclosed are D-peptide compositions and methods for inhibiting HIV entry into host cells.

21 Claims, 10 Drawing Sheets

Specification includes a Sequence Listing.

(51) Int. Cl.
| | |
|---|---|
| A61K 38/10 | (2006.01) |
| C07K 7/08 | (2006.01) |
| A61K 47/60 | (2017.01) |
| A61K 47/54 | (2017.01) |
| A61P 31/18 | (2006.01) |
| A61K 38/00 | (2006.01) |

(52) U.S. Cl.
CPC ............. *A61K 47/554* (2017.08); *A61K 47/60* (2017.08); *A61P 31/18* (2018.01); *C07K 7/08* (2013.01); *A61K 38/00* (2013.01)

(56) References Cited

U.S. PATENT DOCUMENTS

| | | |
|---|---|---|
| 6,841,657 B2 | 1/2005 | Eckert et al. |
| 7,129,227 B1 | 10/2006 | Kucera et al. |
| 9,381,226 B2 | 7/2016 | Kay et al. |
| 2011/0027183 A1 | 2/2011 | Mier et al. |
| 2014/0323392 A1 | 10/2014 | Francis et al. |
| 2016/0354428 A1 | 12/2016 | Kay et al. |
| 2017/0239364 A1 | 8/2017 | Francis et al. |

FOREIGN PATENT DOCUMENTS

| | | |
|---|---|---|
| WO | 2008/098182 A1 | 8/2008 |
| WO | 2009/092612 A1 | 7/2009 |
| WO | 2012/135385 A1 | 10/2012 |
| WO | 2017/040350 A1 | 3/2017 |

OTHER PUBLICATIONS

Brünger et al., "Crystallography & NMR System: A New Software Suite for Macromolecular Structure Determination," *Acta Crystallographica* D54(5):905-921, 1998.
Chan et al., "Core Structure of gp41 from the HIV Envelope Glycoprotein," *Cell* 89(2):263-273, 1997.
Chan et al., "Evidence that a prominent cavity in the coiled coil of HIV type 1 gp41 is an attractive drug target," *Proceedings of the National Academy of Sciences of the United States of America* 95(26):15613-15617, 1998.
Chan et al., "HIV Entry and Its Inhibition," *Cell* 93(5):681-684, 1998.
Cheng et al., "Enhanced Hepatic Uptake and Bioactivity of Type α1(I) Collagen Gene Promoter-Specific Triplex-Forming Oligonucleotides after Conjugation with Cholesterol," *Journal of Pharmacology and Experimental Therapeutics* 317(2):797-805, 2006.
Chong et al., "Comparative immunological properties of enantiomeric peptides," *Letters in Peptide Science* 3(2):99-106, 1996.
Choudhry et al., "Increased Efficacy of HIV-1 Neutralization by Antibodies at Low CCR5 Surface Concentration," *Biochemical and Biophysical Research Communications* 348(3):1107-1115, 2006. (16 pages).
Cole et al., "Thermodynamics of Peptide Inhibitor Binding to HIV-1 gp41," *Biochemistry* 40(19):5633-5641, 2001.
Collaborative Computational Project, No. 4, "The CCP4 Suite: Programs for Protein Crystallography," *Acta Crystallographica* D50(5): 760-763, 1994. (5 pages).
Debnath et al., "Structure-Based Identification of Small Molecule Antiviral Compounds Targeted to the gp41 Core Structure of the Human Immunodeficiency Virus Type 1," *Journal of Medicinal Chemistry* 42(17):3203-3209, 1999.
Denton et al., "One Percent Tenofovir Applied Topically to Humanized BLT Mice and Used According to the CAPRISA 004 Experimental Design Demonstrates Partial Protection from Vaginal HIV Infection, Validating the BLT Model for Evaluation of New Microbicide Candidates," *Journal of Virology* 85(15):7582-7593, 2011.
Eckert et al., "Design of potent inhibitors of HIV-1 entry from the gp41 N-peptide region," *Proceedings of the National Academy of Sciences of the United States of America* 98(20):11187-11192, 2001.
Eckert et al., "Inhibiting HIV-1 Entry: Discovery of D-Peptide Inhibitors that Target the gp41 Coiled-Coil Pocket," *Cell* 99(1):103-115, 1999.
Eckert et al., "Mechanisms of Viral Membrane Fusion and Its Inhibition," *Annual Review of Biochemistry* 70:777-810, 2001. (36 pages).
Emsley et al., "Coot: model-building tools for molecular graphics," *Acta Crystallographica* D60(12):2126-2132, 2004.
Ernst et al., "Design of a Protein Surface Antagonist Based on α-Helix Mimicry: Inhibition of gp41 Assembly and Viral Fusion," *Angewandte Chemie International Edition* 41(2):278-281, 2002.
Extended European Search Report, dated Apr. 23, 2010, for European Application No. 08729413, 14 pages.
Extended European Search Report, dated Apr. 23, 2013, for European Application No. 13156450, 9 pages.
Extended European Search Report, dated Nov. 4, 2014, for European Application No. 12763412, 8 pages.
Ferrer et al., "Selection of gp41-mediated HIV-1 cell entry inhibitors from biased combinatorial libraries of non-natural binding elements," *Nature Structural Biology* 6(10):953-960, 1999.
Final Office Action, dated Dec. 19, 2013, for U.S. Appl. No. 12/526,071, Kay et al., "Methods and Compositions Related to Inhibition of Viral Entry," 5 pages.
Final Office Action, dated Jan. 29, 2016, for U.S. Appl. No. 14/007,785, Francis et al., "Methods and Compositions Related to Inhibition of Viral Entry," 15 pages.
Final Office Action, dated Oct. 18, 2018, for U.S. Appl. No. 15/171,753, Kay et al., "Methods and Compositions Related to Inhibition of Viral Entry," 13 pages.
Final Office Action, dated Oct. 28, 2015, for U.S. Appl. No. 12/526,071, Kay et al., "Methods and Compositions Related to Inhibition of Viral Entry," 7 pages.
Francis et al., "Design of a modular tetrameric scaffold for the synthesis of membrane-localized D-peptide inhibitors of HIV-1 entry," *Bioconjugate Chemistry* 23(6):1252-1258, 2012. (15 pages).
Francis et al., "Preclinical Characterization of a Potent D-Peptide Inhibitor of HIV Entry: Cholesterol-conjugated PIE12-trimer," *HIV Research for Prevention Conference*, Chicago, Illinois, USA, Oct. 17-21, 2016, 1 page. (poster).
Frey et al., "Small molecules that bind the inner core of gp41 and inhibit HIV envelope-mediated fusion," *Proceedings of the National Academy of Sciences of the United States of America* 103(38):13938-13943, 2006.
Furuta et al., "Capture of an early fusion-active conformation of HIV-1 gp41," *Nature Structural Biology* 5(4):276-279, 1998. (5 pages).
Gait et al., "Progress in anti-HIV structure-based drug design," *Trends in Biotechnology* 13(10):430-438, 1995.
Gali et al., "In Vitro Evaluation of Viability, Integrity, and Inflammation in Genital Epithelia upon Exposure to Pharmaceutical Excipients and Candidate Microbicides," *Antimicrobial Agents and Chemotherapy* 54(12):5105-5114, 2010.
Gallo et al., "The Stability of the Intact Envelope Glycoproteins Is a Major Determinant of Sensitivity of HIV/SIV to Peptidic Fusion Inhibitors," *Journal of Molecular Biology* 340(1):9-14, 2004.
Hamburger et al., "Steric Accessibility of the HIV-1 gp41 N-trimer Region," *The Journal of Biological Chemistry* 280(13):12567-12572, 2005. (7 pages).
Harris et al., "Effect of Pegylation on Pharmaceuticals," *Nature Reviews Drug Discovery* 2(3):214-221, 2003.
Huet et al., "Long-Lasting Enfuvirtide Carrier Pentasaccharide Conjugates with Potent Anti-Human Immunodeficiency Virus Type 1 Activity," *Antimicrobial Agents and Chemotherapy* 54(1):134-142, 2010.
Ingallinella et al., "Addition of a cholesterol group to an HIV-1 peptide fusion inhibitor dramatically increases its antiviral potency," *Proceedings of the National Academy of Sciences of the United States of America* 106(14):5801-5806, 2009.
International Preliminary Report on Patentability, dated Aug. 11, 2009, for International Application No. PCT/US2008/053447, 4 pages.
International Preliminary Report on Patentability, dated Jul. 10, 2018, for International Application No. PCT/US2017/012640, 7 pages.

(56) References Cited

OTHER PUBLICATIONS

International Preliminary Report on Patentability, dated Oct. 1, 2013, for International Application No. PCT/US2012/031015, 9 pages.
International Search Report and Written Opinion, dated Apr. 7, 2017, for International Application No. PCT/US2017/012640, 11 pages.
International Search Report and Written Opinion, dated Aug. 10, 2012, for International Application No. PCT/US2012/031015, 14 pages.
International Search Report and Written Opinion, dated May 8, 2008, for International Application No. PCT/US2008/053447, 5 pages.
Jiang et al., "HIV-1 inhibition by a peptide," *Nature* 365(6442):113, 1993.
Jiang et al., "N-Substituted Pyrrole Derivatives as Novel Human Immunodeficiency Virus Type 1 Entry Inhibitors That Interfere with the gp41 Six-Helix Bundle Formation and Block Virus Fusion," *Antimicrobial Agents and Chemotherapy* 48(11):4349-4359, 2004. (12 pages).
Jin et al., "Design of a Peptide Inhibitor that Blocks the Cell Fusion Mediated by Glycoprotein 41 of Human Immunodeficiency Virus Type 1," *AIDS Research and Human Retroviruses* 16(17):1797-1804, 2000.
Judice et al., "Inhibition of HIV type 1 infectivity by constrained α-helical peptides: Implications for the viral fusion mechanism," *Proceedings of the National Academy of Sciences of the United States of America* 94(25):13426-13430, 1997.
Kay, "Design and Preclinical Characterization of a D-Peptide HIV Entry Inhibitor," *HIV Research for Prevention Conference*, Chicago, Illinois, USA, Oct. 17-21, 2016, 4 pages.
Louis et al., "Covalent Trimers of the Internal N-terminal Trimeric Coiled-coil of gp41 and Antibodies Directed against Them Are Potent Inhibitors of HIV Envelope-mediated Cell Fusion," *The Journal of Biological Chemistry* 278(22):20278-20285, 2003.
Lu et al., "A trimeric structural domain of the HIV-1 transmembrane glycoprotein," *Nature Structural Biology* 2(12):1075-1082, 1995.
McCoy et al., "Likelihood-enhanced fast translation functions," *Acta Crystallographica* D61(4):458-464, 2005.
Miller et al., "A human monoclonal antibody neutralizes diverse HIV-1 isolates by binding a critical gp41 epitope," *Proceedings of the National Academy of Sciences of the United States of America* 102(41):14759-14764, 2005.
Milton et al., "Total Chemical Synthesis of a D-Enzyme: The Enantiomers of HIV-1 Protease Show Demonstration of Reciprocal Chiral Substrate Specificity," *Science* 256(5062):1445-1448, 1992.
Naider et al., "Peptides in the treatment of AIDS," *Current Opinion in Structural Biology* 19(4):473-482, 2009.
Noren et al., "Construction of High-Complexity Combinatorial Phage Display Peptide Libraries," *Methods* 23(2):169-178, 2001.
Notice of Allowance, dated Aug. 27, 2018, for U.S. Appl. No. 15/448,492, Francis et al., "Methods and Compositions Related to Inhibition of Viral Entry," 11 pages.
Office Action, dated Apr. 19, 2018, for Canadian Application No. 2,677,665, 3 pages.
Office Action, dated Apr. 28, 2014, for Canadian Application No. 2,677,665, 6 pages.
Office Action, dated Feb. 24, 2011, for European Application No. 08729413, 6 pages.
Office Action, dated Jan. 30, 2014, for European Application No. 13156450, 5 pages.
Office Action, dated Jul. 19, 2016, for European Application No. 12763412, 4 pages.
Office Action, dated Jun. 2, 2015, for Canadian Application No. 2,677,665, 4 pages.
Office Action, dated Mar. 12, 2018, for Canadian Application No. 2,868,735, 6 pages.
Office Action, dated Mar. 15, 2016, for Japanese Application No. 2014-502764, 5 pages. (English Translation).
Office Action, dated Mar. 30, 2015, for European Application No. 13156450, 5 pages.
Office Action, dated May 26, 2016, for Canadian Application No. 2,677,665, 3 pages.
Office Action, dated May 4, 2017, for Canadian Application No. 2,677,665, 3 pages.
Office Action, dated Oct. 12, 2018, for Canadian Application No. 2,868,735, 4 pages.
Office Action, dated Oct. 25, 2016, for Japanese Application No. 2014-502764, 3 pages. (English Translation).
Office Action, dated Sep. 1, 2015, for European Application No. 12763412, 5 pages.
Office Action, dated Dec. 28, 2017, for U.S. Appl. No. 15/171,753, Kay et al., "Methods and Compositions Related to Inhibition of Viral Entry," 8 pages.
Office Action, dated Feb. 27, 2013, for U.S. Appl. No. 12/526,071, Kay et al., "Methods and Compositions Related to Inhibition of Viral Entry," 6 pages.
Office Action, dated Jun. 22, 2015, for U.S. Appl. No. 14/007,785, Francis et al., "Methods and Compositions Related to Inhibition of Viral Entry," 14 pages.
Office Action, dated Mar. 2, 2015, for U.S. Appl. No. 12/526,071, Kay et al., "Methods and Compositions Related to Inhibition of Viral Entry," 6 pages.
Office Action, dated Nov. 16, 2017, for U.S. Appl. No. 15/448,492, Francis et al., "Methods and Compositions Related to Inhibition of Viral Entry," 23 pages.
Office Action, dated Sep. 2, 2016, for U.S. Appl. No. 14/007,785, Francis et al., "Methods and Compositions Related to Inhibition of Viral Entry," 18 pages.
Ogura et al., "A Novel Active Ester Synthesis Reagent (N,N'-Disuccinimidyl Carbonate)," *Tetrahederon Letters* 20(49):4745-4746, 1979.
Otwinowski et al., "Processing of X-Ray Diffraction Data Collected in Oscillation Mode," *Methods in Enzymology* 276:307-326, 1997.
Pappenheimer et al., "Absorption and Excretion of Undegradable Peptides: Role of Lipid Solubility and Net Charge," *The Journal of Pharmacology and Experimental Therapeutics* 280(1):292-300, 1997.
Pappenheimer et al., "Intestinal absorption and excretion of octapeptides composed of D amino acids," *Proceedings of the National Academy of Sciences of the United States of America* 91(5):1942-1945, 1994.
Platt et al., "Kinetic Factors Control Efficiencies of Cell Entry, Efficacies of Entry Inhibitors, and Mechanisms of Adaptation of Human Immunodeficiency Virus," *Journal of Virology* 79(7):4347-4356, 2005. (11 pages).
Redman et al., "Pharmacokinetic and Chemical Synthesis Optimization of a Potent D-Peptide HIV Entry Inhibitor Suitable for Extended-Release Delivery," *Molecular Pharmaceutics* 15(3):1169-1179, 2018.
Requirement for Restriction/Election, dated Apr. 27, 2012, for U.S. Appl. No. 12/526,071, Kay et al., "Methods and Compositions Related to Inhibition of Viral Entry," 9 pages.
Requirement for Restriction/Election, dated Jun. 1, 2017, for U.S. Appl. No. 15/448,492, Francis et al., "Methods and Compositions Related to Inhibition of Viral Entry," 6 pages.
Requirement for Restriction/Election, dated Mar. 28, 2017, for U.S. Appl. No. 15/171,753, Kay et al., "Methods and Compositions Related to Inhibition of Viral Entry," 6 pages.
Requirement for Restriction/Election, dated Oct. 23, 2014, for U.S. Appl. No. 14/007,785, Francis et al., "Methods and Compositions Related to Inhibition of Viral Entry," 10 pages.
Rimsky et al., "Determinants of Human Immunodeficiency Virus Type 1 Resistance to gp41-Derived Inhibitory Peptides," *Journal of Virology* 72(2):986-993, 1998.
Root et al., "Protein Design of an HIV-1 Entry Inhibitor," *Science* 291(5505):884-888, 2001.
Root et al., "HIV-1 gp41 as a Target for Viral Entry Inhibition," *Current Pharmaceutical Design* 10(15):1805-1825, 2004. (22 pages).
Sadowski et al., "A Synthetic Peptide Blocking the Apolipoprotein E/β-Amyloid Binding Mitigates β-Amyloid Toxicity and Fibril Formation in Vitro and Reduces β-Amyloid Plaques in Transgenic Mice," *American Journal of Pathology* 165(3):937-948, 2004.

(56) References Cited

OTHER PUBLICATIONS

Schumacher et al., "Identification of D-Peptide Ligands Through Mirror-Image Phage Display," *Science* 271(5257):1854-1857, 1996.
Scott et al., "Phage-display Vectors," in *Phage Display: A Laboratory Manual*, Cold Springs Harbor Laboratory Press, New York City, New York, USA, 2001, pp. 2.1-2.19. (20 pages).
Sia et al., "Short constrained peptides that inhibit HIV-1 entry," *Proceedings of the National Academy of Sciences of the United States of America* 99(23):14664-14669, 2002.
Sidhu et al., "Phage Display for Selection of Novel Binding Peptides," *Methods in Enzymology* 328:333-363, 2000. (32 pages).
Steger et al., "Kinetic Dependence to HIV-1 Entry Inhibition," *The Journal of Biological Chemistry* 281(35):25813-25821, 2006. (10 pages).
Stephens et al., "Inhibiting HIV Fusion with a β-Peptide Foldamer," *Journal of the American Chemical Society* 127(38):13126-13127, 2005. (6 pages).
Tan et al., "Atomic structure of a thermostable subdomain of HIV-1 gp41," *Proceedings of the National Academy of Sciences of the United States of America* 94(23):12303-12308, 1997.
Wei et al., "Emergence of Resistant Human Immunodeficiency Virus Type 1 in Patients Receiving Fusion Inhibitor (T-20) Monotherapy," *Antimicrobial Agents and Chemotherapy* 46(6):1896-1905, 2002. (11 pages).
Weinstock et al., "Protease-Resistant Peptide Design—Empowering Nature's Fragile Warriors Against HIV," *Biopolymers* 98(5):431-442, 2012. (19 pages).
Weissenhorn et al., "Atomic structure of the ectodomain from HIV-1 gp41," *Nature* 387(6631):426-430, 1997.
Welch et al., "Design of a Potent d-Peptide HIV-1 Entry Inhibitor with a Strong Barrier to Resistance," *Journal of Virology* 84(21):11235-11244, 2010. (11 pages).
Welch et al., "Potent D-peptide inhibitors of HIV-1 entry," *Proceedings of the National Academy of Sciences of the United States of America* 104(43):16828-16833, 2007.
Wild et al., "A synthetic peptide inhibitor of human immunodeficiency virus replication: Correlation between solution structure and viral inhibition," *Proceedings of the National Academy of Sciences of the United States of America* 89(21):10537-10541, 1992.
Wild et al., "Peptides corresponding to a predictive α-helical domain of human immunodeficiency virus type 1 gp41 are potent inhibitors of virus infection," *Proceedings of the National Academy of Sciences of the United States of America* 91(21):9770-9774, 1994.
Zhang et al., "Multiple-Peptide Conjugates for Binding β-Amyloid Plaques of Alzheimer's Disease," *Bioconjugate Chemistry* 14(1):86-92, 2003.
Zhao et al., "XTT Formazan Widely Used to Detect Cell Viability Inhibits HIV Type 1 Infection in Vitro by Targeting gp41," *AIDS Research and Human Retroviruses* 18(14):989-997, 2002.
Eckert et al, "Characterization of the steric defense of the HIV-1 gp41 N-trimer region," *Protein Sci.* 17(12):2091-2100, 2008.
Kim et al., "Peptide Mimic of the HIV Envelope gp120-gp41 Interface," *Journal of Molecular Biology* 376(3):786-797, 2008.
Kol et al., "A Stiffness Switch in Human Immunodeficiency Virus," *Biophys. J.* 92:1777-1783, 2007.
Kol et al., "The effect of purification method on the completeness of the immature HIV-1 Gag shell," *J. Virol. Methods* 169:244-247, 2010.
Pang et al., "Virion stiffness regulates immature HIV-1 entry," *Retrovirology* 10:4, 2013. (11 pages).
Welch et al., "Discovery and Design of Potent D-Peptide Inhibitors of HIV-1 Entry," *West Coast Retrovirus Meeting*, Palm Springs, California, Oct. 2007. (20 pages).

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: synthetic D-peptide
<220> FEATURE:
<221> NAME/KEY: AMIDATION
<222> LOCATION: 1
<220> FEATURE:
<221> NAME/KEY: ACETYLATION
<222> LOCATION: 16

<400> SEQUENCE: 1

His Pro Cys Asp Tyr Pro Glu Trp Gln Trp Leu Cys Glu Leu Gly Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetic D-peptide
<220> FEATURE:
<221> NAME/KEY: ACETYLATION
<222> LOCATION: 1
<220> FEATURE:
<221> NAME/KEY: MOD_RES
<222> LOCATION: 16
<223> OTHER INFORMATION: PEG4 linked to Lys side chain
<220> FEATURE:
<221> NAME/KEY: AMIDATION
<222> LOCATION: 16

<400> SEQUENCE: 2

His Pro Cys Asp Tyr Pro Glu Trp Gln Trp Leu Cys Glu Leu Gly Lys
1               5                   10                  15

<210> SEQ ID NO 3
<211> LENGTH: 16
<212> TYPE: PRT
<213> ORGANISM: Artificial Sequence
<220> FEATURE:
```

```
<223> OTHER INFORMATION: synthetic D-peptide
<220> FEATURE:
<221> NAME/KEY: ACETYLATION
<222> LOCATION: 1
<220> FEATURE:
<221> NAME/KEY: MOD_RES
<222> LOCATION: 15
<223> OTHER INFORMATION: PEG4 inserted directly into peptide backbone
      between Gly and Lys at Positions 15-16
<220> FEATURE:
<221> NAME/KEY: AMIDATION
<222> LOCATION: 16

<400> SEQUENCE: 3

His Pro Cys Asp Tyr Pro Glu Trp Gln Trp Leu Cys Glu Leu Gly Lys
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: synthetic D-peptide
<220> FEATURE:
<221> NAME/KEY: VARIANT
<222> LOCATION: (1)...(5)
<223> OTHER INFORMATION: Xaa = Any naturally occuring amino acid

<400> SEQUENCE: 4

Glu Trp Xaa Trp Leu
1               5

<210> SEQ ID NO 5
<211> LENGTH: 4
<212> TYPE: PRT
<213> ORGANISM: Artificial Sequence
<220> FEATURE:
<223> OTHER INFORMATION: synthetic D-peptide
<220> FEATURE:
<221> NAME/KEY: VARIANT
<222> LOCATION: (1)...(4)
<223> OTHER INFORMATION: Xaa = Any naturally occuring amino acid

<400> SEQUENCE: 5

Trp Xaa Trp Leu
1

<210> SEQ ID NO 6
<211> LENGTH: 16
<212> TYPE: PRT
<213> ORGANISM: Artificial Sequence
<220> FEATURE:
<223> OTHER INFORMATION: synthetic D-peptide
<220> FEATURE:
<221> NAME/KEY: MOD_RES
<222> LOCATION: 15
<223> OTHER INFORMATION: PEG4 inserted directly into peptide backbone
      between Gly and Lys at Positions 15-16

<400> SEQUENCE: 6

His Pro Cys Asp Tyr Pro Glu Trp Gln Trp Leu Cys Glu Leu Gly Lys
1               5                   10                  15
```

D-PEPTIDE INHIBITORS OF HIV ENTRY AND METHODS OF USE

STATEMENT REGARDING FEDERALLY SPONSORED RESEARCH

This invention was made with government support under grant numbers GM066521 and AI076168 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690181_405WO_SEQUENCE_LISTING.txt. The text file is 2.4 KB, was created on Jan. 5, 2017, and is being submitted electronically via EFS-Web.

BACKGROUND

HIV entry is mediated by the viral envelope glycoprotein, which comprises non-covalently associated surface (gp120) and transmembrane (gp41) subunits. Gp120 is primarily involved in recognition of cellular receptors, while gp41 directly mediates membrane fusion. When peptides isolated from the gp41 N- and C-peptide regions (N- and C-peptides) are mixed in solution, they form a six-helix bundle, which represents the post-fusion gp41 structure. Three N-peptides form a central parallel trimeric coiled coil (N-trimer) surrounded by three antiparallel helical C-peptides that nestle into long grooves between neighboring N-peptides. The importance of this structure is indicated by the dominant negative inhibition of HIV entry by N- and C-peptides.

The available inhibitory and structural data support a working model of HIV membrane fusion (FIG. 1). Initially, gp120 interacts with cellular CD4 and a chemokine coreceptor (typically CXCR4 or CCR5), causing large conformational changes in gp120 that propagate to gp41 via the gp41-gp120 interface. Gp41 then undergoes a structural rearrangement that unleashes its N-terminal fusion peptide, which embeds in the target cell membrane. At this stage of fusion, gp41 adopts an extended "prehairpin intermediate" conformation that bridges both viral and cellular membranes and exposes the N-trimer region. This intermediate is relatively long-lived (minutes), but ultimately collapses as the N- and C-peptide regions of each gp41 monomer associate to form a hairpin structure. Three such hairpins (trimer-of-hairpins) form the 6-helix bundle, which forces the viral and cellular membranes into tight apposition and leads to membrane fusion. This structure likely corresponds to the core of the fusion-active state of gp41 and shows similarity to the proposed fusogenic structures of envelope fusion proteins from influenza, Moloney Murine Leukemia Virus, and simian immunodeficiency virus (SIV), and Ebola virus.

According to this model, an inhibitor that binds to the N-trimer and prevents hairpin formation can inhibit viral entry. This has been well supported by the discovery of numerous peptide, protein, and small molecule inhibitors that bind the N-trimer. A particularly interesting feature of the N-trimer is the deep hydrophobic "pocket" formed by its 17 C-terminal residues. This pocket has several enticing features as an inhibitory target including: (1) a very highly conserved sequence, (2) an essential role in viral entry, (3) a compact binding site vulnerable to inhibition by short peptides, and (4) the availability of several designed peptides (e.g., IQN17, IZN17, 5-helix, NCCGN13 that authentically mimic the pocket structure). There is a need in the art for peptides with suitable pharmacokinetic properties that can potently inhibit the entry of HIV into host cells. The present disclosure provides approaches and embodiments addressing such needs and further provides other related advantages.

BRIEF SUMMARY

Embodiment 1. A composition comprising at least one PIE12-2 D-peptide comprising SEQ ID NO:3 [HPCDYPEWQWLCELG-(PEG$_4$)-K], wherein the at least one PIE12-2 D-peptide interacts with the N-trimer pocket of HIV gp41.

Embodiment 2. The composition of embodiment 1, comprising at least two PIE12-2 D-peptides comprising SEQ ID NO:3 [HPCDYPEWQWLCELG-(PEG$_4$)-K].

Embodiment 3. The composition of embodiment 1, comprising at least three PIE12-2 D-peptides comprising SEQ ID NO:3 [HPCDYPEWQWLCELG-(PEG$_4$)-K].

Embodiment 4. The composition of any one of embodiments 1-3, wherein each PIE12-2 D-peptide is linked to an arm of a multimer scaffold comprising three arms via an amide bond between the epsilon amino group of the C-terminal D-lysine of the PIE12-2 D-peptide and a carboxyl group of the arm of the multimer scaffold, wherein the multimer scaffold is based on 4-Amino-4-(2-carboxyethyl) heptanedioic acid.

Embodiment 5. The composition of embodiment 4, wherein each PIE12-2 D-peptide and linkage to the multimer scaffold is as shown in FIG. 4B.

Embodiment 6. The composition of embodiment 4 or 5, further comprising a fourth arm linking a cholesterol moiety via a polyethylene glycol (PEG) linker to the multimer scaffold, wherein the total number of ethylene glycol repeats in the fourth arm ranges from 12-132.

Embodiment 7. The composition of embodiment 6, wherein the total number of ethylene glycol repeats in the fourth arm ranges from 24-48.

Embodiment 8. The composition of embodiment 6 or 7, wherein the PEG linker comprises a first PEG chain and a second PEG chains in series linking the cholesterol moiety to the multimer scaffold.

Embodiment 9. The composition of any one of embodiments 6-8, wherein the total number of ethylene glycol repeats in the fourth arm is 32.

Embodiment 10. The composition of embodiment 8, wherein the first PEG chain comprises 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 ethylene glycol repeats and the second PEG chain comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 ethylene glycol repeats, respectively.

Embodiment 11. The composition of embodiment 10, wherein the first PEG chain comprises 28 ethylene glycol repeats and the second PEG chain comprises 4 ethylene glycol repeats.

Embodiment 12. The composition of any one of embodiments 5-11, wherein the PEG linker is linked to the multimer scaffold via an amide bond.

Embodiment 13. The composition of any one of embodiments 8-12, wherein the second PEG chain is linked to the first PEG chain via an amide bond.

Embodiment 14. The composition of embodiment 12 or 13, wherein the first or second PEG chain comprises an NHS ester group for creating the amide bond linkage.

Embodiment 15. The composition of any one of embodiments 5-14, wherein the cholesterol moiety is linked to the PEG linker via a carbamate linkage.

Embodiment 16. The composition of embodiment 15, wherein the cholesterol moiety is cholesteryl chloroformate.

Embodiment 17. The composition of any one of embodiments 8-16, wherein the first PEG chain is linked to the multimer scaffold prior to linking of the cholesterol moiety and second PEG chain.

Embodiment 18. The composition of embodiments 17, wherein after linking the first PEG chain to the multimer scaffold, the composition is purified prior to linking of the cholesterol moiety and second PEG chain.

Embodiment 19. The composition of any one of embodiments 5-18, wherein addition of the cholesterol moiety to the fourth arm does not create stereoisomers. Embodiment 20. The composition of any one of embodiments 8-19, wherein the cholesterol moiety is attached to fourth arm of the multimer scaffold via the second PEG chain and is cholesteryl-PEG4-NHS ester as shown in the following figure:

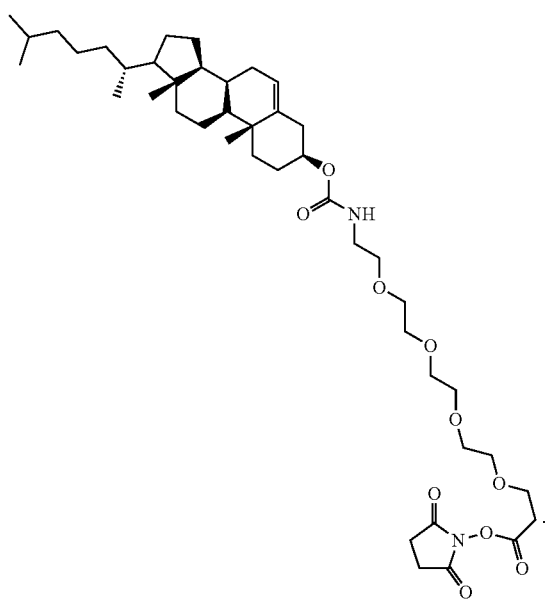

Embodiment 21. The composition of embodiment 6, comprising at least one trimeric PIE12-2 D-peptide-cholesterol conjugate having the following structure:

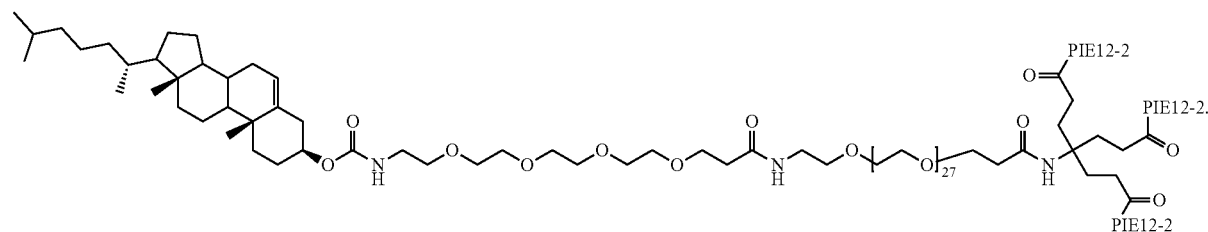

Embodiment 22. A pharmaceutical composition comprising a composition of any one of embodiments 1-21 and a pharmaceutical carrier.

Embodiment 23. The composition of any one of embodiments 1-22, further comprising at least one anti-viral agent selected from a viral replication inhibitor, a viral protease inhibitor, a viral reverse transcriptase inhibitor, a viral entry inhibitor, a viral integrase inhibitor, a viral Rev inhibitor, a viral Tat inhibitor, a viral Nef inhibitor, a viral Vpr inhibitor, a viral Vpu inhibitor, and a viral Vif inhibitor.

Embodiment 24. A method of inhibiting HIV entry into a host cell comprising exposing the virus to a composition of any one of embodiments 1-23, thereby inhibiting HIV entry into the host cell.

Embodiment 25. A method of treating HIV infection in a subject comprising administering to the subject an effective amount of a composition of any one of embodiments 1-24, thereby treating HIV infection.

Embodiment 26. A method of synthesizing a trimeric D-peptide-cholesterol conjugate of the following structure, PIE12-2 D-peptides are conjugated to the scaffold via reaction of the NHS ester on the scaffold to the unique primary amine of the PIE12-2 peptide located on the side chain of the C-terminal lysine residue to yield an FMOC-PEG28-PIE12-2 trimer. In step (5), the FMOC protecting group is removed from the FMOC-PEG28-PIE12-2 trimer using piperdine to yield NH2-PEG28-PIE12-2 trimer. In step (6), the NH2-PEG28-PIE12-2 trimer is conjugated to cholesteryl-PEG4-NHS, yielding CPT31.

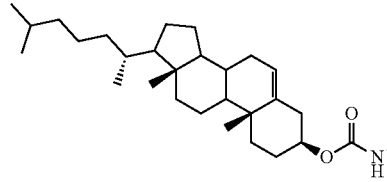
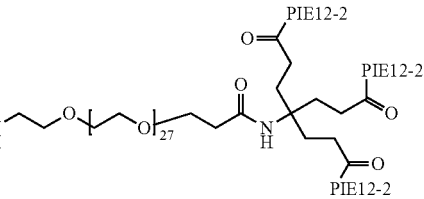

wherein the method comprises the steps as set forth in FIG. 6.

DETAILED DESCRIPTION

Figure 1:
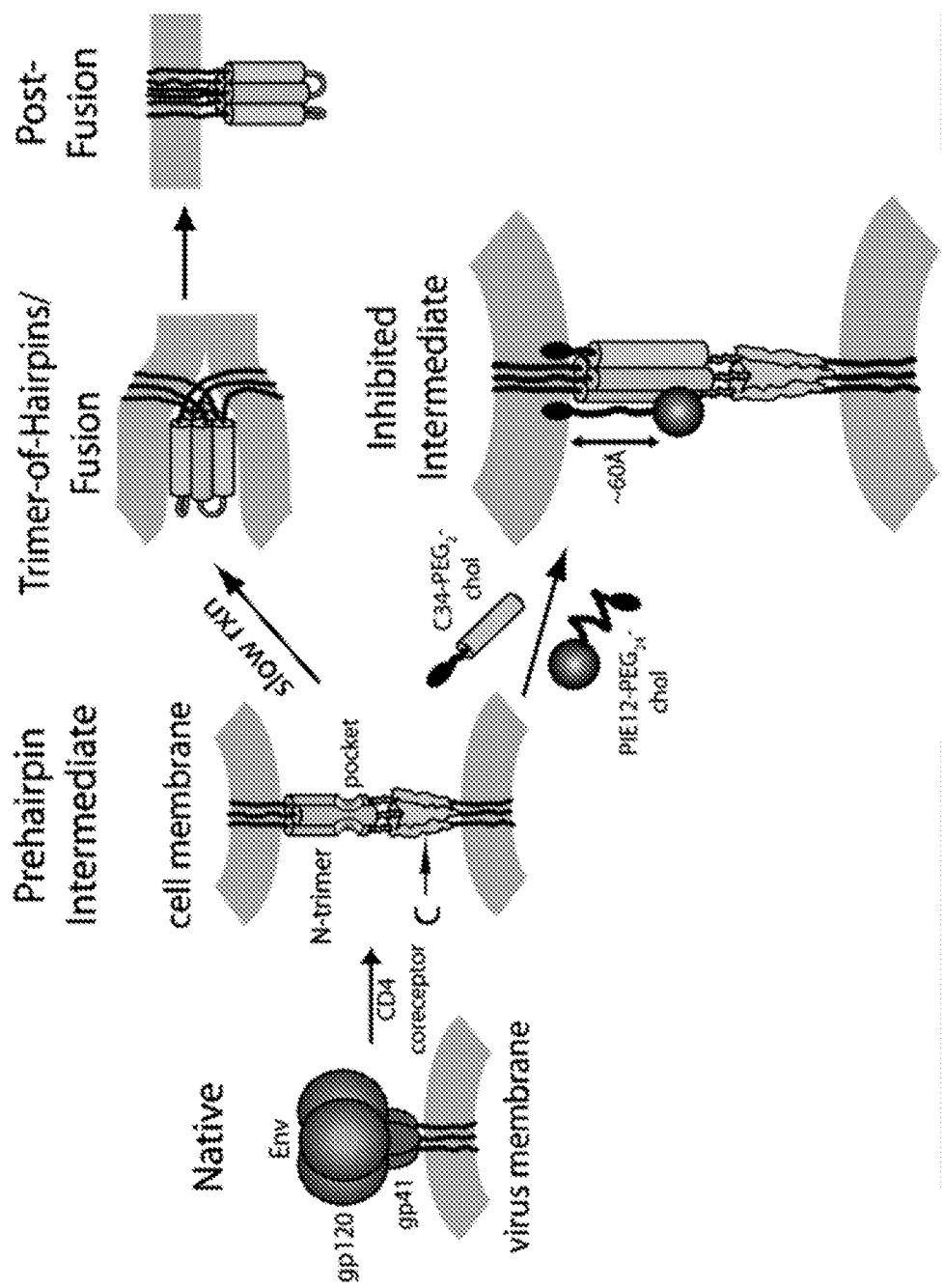
FIG. 1 depicts an embodiment of a HIV entry pathway. The gp41 fusion peptide and transmembrane domain are also down. For clarity, gp120 is omitted from the prehairpin intermediate.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a polypeptide is disclosed and discussed and a number of modifications that can be made to a number of molecules including the polypeptide are discussed, each and every combination and permutation of polypeptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Disclosed are the components to be used to prepare the disclosed compositions as well as the compositions themselves to be used within the methods disclosed herein.

Synthetic C-peptides (peptides corresponding to the C-helix), such as DP178 and C34, are potent inhibitors of HIV-1 membrane fusion and are effective against both laboratory-adapted strains and primary isolates. Based on the structural features of the gp41 core, these peptides are thought to act through a dominant-negative mechanism, in which exogenous C-peptides bind to the central coiled-coil of gp41 and lead to its inactivation. These peptides likely act on a pre-hairpin intermediate of gp41 that forms when the native gp41 structure (i.e., the nonfusogenic conformation present on free virions) is perturbed by gp120/CD4/coreceptor interactions. This pre-hairpin intermediate has an exposed N-coiled-coil, thereby allowing C-peptides to bind and inactivate gp41 prior to the formation of the fusion-active hairpin structure. Therefore, compounds that bind with high affinity to this cavity and prevent normal N- and C-helix pairing are effective HIV-1 inhibitors. In addition, residues in the cavity are highly conserved among diverse HIV-1 isolates. Because of the high structural conservation, drugs targeting this site would have broad activity against diverse HIV isolates.

As described herein, the pocket on the surface of the N-helix coiled-coil of HIV-1 envelope protein gp41 subunit is a drug target. Similarly, cavities on other pathogens (e.g., HIV-2) which can cause AIDS or on pathogens which cause AIDS-like conditions in nonhuman mammals (e.g., SIV) are also drug targets. Available methods (e.g., mirror image phage display methods, combinational chemistry, computational approaches and other drug screening and medicinal chemistry methods) can be used to identify peptides, D-peptides, including multimers, and peptidomimetics and small molecules that bind the coiled-coil cavity of HIV-1 (and/or HIV-2) with sufficient affinity to interfere with viral entry into cells and, thus, inhibit viral infection. Mirror image phage display has been used to identify D-peptides which bind to a cavity on the surface of the N-helix coiled-coil of HIV-1 gp41.

Compositions

Peptides

Disclosed herein are compositions comprising at least one improved D-peptide (e.g., PIE12-2) that interacts with the N-trimer pocket of HIV gp41. For example, the D-peptides can bind to a cavity on the surface of the N-helix coiled-coil of HIV envelope glycoprotein gp41 (e.g., HIV-1, HIV-2). Such D-peptides can be of any length, provided that they are of sufficient length to bind the cavity in such a manner that they interfere with the interaction of the N-helix coiled-coil cavity and amino acid residues of the C-peptide region of viral gp41 and prevent, or inhibit, viral entry into the cells. For example, the peptide can comprise at least 2, 3, 4, 5, 6, 7, 8, 9, or 10 core amino acid residues in length. The amino acid residues can be naturally occurring or non-naturally occurring or modified, as described herein. Examples of peptides that bind the N-trimer of HIV gp41 may be found in U.S. Patent Publications 2010/0184663 and 2014/0323392, each of which is incorporated in its entirety by reference herein.

D-peptides are peptides that are of the opposite handedness from the handedness of naturally-occurring peptides. Consequently, D-peptides do not serve as efficient substrates for enzymes, and, therefore, are not as readily degraded as L-peptides. In addition, there is no known effective immune response which targets D-peptides and therefore, they do not elicit an immune response comparable to that elicited by L amino acid peptides. Furthermore, D-peptides have several potential advantages over L-peptide including: (1) D-peptides are resistant to proteases, a property that can dramatically increase serum half-life, (2) L-peptides must be injected to avoid digestion, but short D-peptides can be absorbed systemically when taken orally, and (3) D-peptides represent a rich source of structural diversity because they can bind to targets with unique interface geometries not available to L-peptides.

Examples of D-peptides, identified as described herein, are shown below. In certain embodiments, D-peptides are referred to as Pocket-specific Inhibitors of Entry (PIE). An example of such a D-peptide inhibitor is PIE12-2, which is represented by the sequence Ac-HPCDYPEWQWLCELG-PEG$_4$-K—NH$_2$ (SEQ ID NO: 3), which is an improved variant of PIE12 and PIE12-PEG4, which have been previously described (see, U.S. Patent Publications 2010/0184663 and 2014/0323392). In certain embodiments, one or more N-terminal lysine residues may be added to a D-peptide to improve water solubility. Particular embodiments of the D-peptides disclosed herein may be shown with the linker sequence "PEG" before the amino acid sequence.

Disclosed in Table 1 are various examples of D-peptides that can be used with the methods and compositions disclosed herein.

TABLE 1

PIE12 D-peptides

| Peptide Name | Sequence (all D-amino acids) | SEQ ID NO: # |
|---|---|---|
| PIE12* | Ac-HPCDYPEWQWLCELGK-NH$_2$ | 1 |
| PIE12-PEG$_4$* | Ac-HPCDYPEWQWLCELGK(PEG$_4$)-NH$_2$ | 2 |
| PIE12-2* | Ac-HPCDYPEWQWLCELG-PEG$_4$-K-NH$_2$ | 3 |

*D-peptides are preferably capped at the N-terminus with an acetyl group ("Ac") and at the C-terminus with an amide ("NH$_2$") group.

The term "D-amino acid residue", as used herein, refers to an a-amino acid residue having the same absolute configuration as D-glyceraldehyde.

Embodiments of the compositions disclosed herein comprise peptides, portions of the peptides, and variations/derivatives of the peptides that can be used as inhibitors of HIV entry into cells. Particular embodiments of the peptides disclosed herein, or a portion of such peptides, that is sufficient to fit into the hydrophobic pocket at the C-terminal end of the coiled-coil and prevent interaction of the C-peptide region with the N-peptide region of gp41, may be useful to inhibit HIV infection. A portion of any of the peptides represented or of a derivative thereof can be from 2 to 20 (any number of residues from 2 to 20) amino acid residues in size. In specific embodiments, D-peptides which comprise at least the consensus sequence EWXWL (SEQ ID NO: 4) or at least the sequence WXWL (SEQ ID NO: 5), can be used. Where D-peptides as described herein include amino acid residues in addition to a consensus sequence, the additional amino acid residues and the size of the D-peptides can be selected with reference to the peptides described herein or can be designed independent of those peptides, provided that peptide can fit into the hydrophobic pocket and act as an inhibitor. Additional amino acid residues can also be present at the N-terminus, the C-terminus or both of the D-peptides described herein, thus producing a larger peptide. Alternatively, there can be other amino acid residues selected, for example, to enhance binding affinity. For example, such a peptide can include the conserved amino acid residues, which can be at the same positions as those at which they occur in the peptides disclosed herein. In some embodiments, the peptide can comprise the core sequence "WXWL" (SEQ ID NO: 5).

In some embodiments of the peptides disclosed herein, the peptides may comprise amino acid residues which can be different from the amino acid residues at these positions in any of the peptides disclosed herein (e.g., can be isoleucine or asparagine or other amino acid residue which does not appear in the peptides disclosed herein) or can be substituted for or replaced by an amino acid residue represented at a specific position in another peptide. Amino acid residues other than the D-versions of the 20 L-amino acids found in natural proteins can be used. Such changes can be made, for example, to enhance bioavailability, binding affinity or other characteristic of the peptide. A D-peptide can comprise the conserved amino acid residues present in the peptides disclosed herein, but they can be separated by fewer (or more) amino acid residues than the number of intervening amino acid residues shown in Table 1. For example, fewer than five amino acid residues can be present between the first cysteine and the glutamic acid in the consensus sequence. Alternatively, these two residues can be separated by more than five amino acid residues. Internal modifications can also be made (e.g., to enhance binding or increase solubility of a peptide). A D-peptide can have additional moieties or amino acids at its N-terminus. For example, a moiety which blocks the N-terminus or gets rid of the charge otherwise present at the N-terminus can be added. The moiety can be, for example, a blocking moiety, such as an acetyl group (Ac) linked directly to the histidine (H), or an acetyl group linked to one or more additional amino acid residues linked to the N-terminal of H, such as an acetyl group linked to one or more lysine residues, which, in turn, are linked to the N-terminal H.

In addition, a D-peptide can have additional and/or altered moieties or amino acids at its C-terminus. For example, the lysine residue at the C-terminus can be altered and/or one or more residues can be added at the C-terminus, for example to enhance binding. Alternatively, functional (chemical) groups other than amino acid residues can be included to produce an inhibitor of the embodiments disclosed herein. For example, these additional chemical groups can be present at the N-terminus, the C-terminus, both termini or internally.

Two or more D-peptides can be linked via an appropriate linker (e.g., a linker of amino acid residues or other chemical moieties) to increase the effectiveness of inhibition. Alternatively, one or more D-peptides can be linked via an appropriate linker to a molecule (drug) that binds to HIV gp120, CD4, CCR5, CXCR4, or a non-pocket region of HIV gp41 to increase the effectiveness of inhibition.

Regarding the nomenclature of the peptides disclosed herein, different families of peptides are referred to as x-mers, where x is considered the number of residues between the cysteine residues. The x-mers are referred to as the "core peptides." For example, the D-peptide of SEQ ID NO: 1 is comprised of 16 residues (HPCDYPEWQWL-CELGK), and so in the standard art would be referred to as a 16-mer. However, in certain embodiments disclosed herein, the length of residues between the cysteines (C) is 8, so it would be considered an 8-mer (and referred to as having 8 core residues), and referred to as such throughout the application. In particular embodiments, amino acids outside of the two Cys residues are referred to as "flanking" sequences. This naming scheme allows different families of peptides that differ in the number of residues between the two Cys residues, but can vary in total peptide length due to differences in their flanking sequences, to be distinguished. For example, the D-peptide of SEQ ID NO: 1 has a length of 16 residues (HPCDYPEWQWLCELGK), is a member of the 8-mer peptide family (as it has 8 core residues), and has an N-terminal flanking sequence of HP and a C-terminal flanking sequence of ELGK. In addition to the core residues and flanking residues present on the peptides disclosed herein, all of the peptides disclosed herein may comprise blocked N- and C-termini. For example, the N-termini may be blocked by an acetyl group (Ac) and the C-termini may be blocked by an amino group (NH$_2$). The acetyl group may represent an N-terminal (acetyl group added as part of the peptide synthesis procedure. The C-terminal amide and the N-terminal acetyl group are preferably components of D-peptides of the present disclosure.

In some embodiments, the D-peptides of the present disclosure can be flanked by "GA" residues at the N-terminus and "AA" residues at the C-terminus, due to the design of the mirror image phage display library used in identifying the D-peptides. Some or all of these amino acid residues may be altered, replaced or deleted in order to produce D-peptides with, for example, altered absorption, distribution, metabolism and/or excretion. In one embodiment, the C-terminus is modified by the addition of a glycine residue immediately before the C-terminal amide. In another embodiment, the most C-terminal "A" is altered/modified or replaced by a different amino acid residue or deleted. In yet a further embodiment, amino acids are added to the C-terminus and/or N-terminus. Thus, it is contemplated herein that the both the N-terminal "GA" residues and C-terminal "AA" residues can substituted or additionally flanked to enhance potency. For example one or two lysines can be added to the C-terminal "AA" residues to create single or double lysine variants of a particular PIE. Also for example, the N-terminal Lys can be modified to comprise "HP" residues at the N-terminus.

An amino acid sequence of a D-peptide contemplated by the present disclosure is HPCDYPEWQWLCELG-PEG$_4$-K (SEQ ID NO:6), and in a preferred embodiment is Ac-HP-CDYPEWQWLCELG-PEG$_4$-K—NH$_2$ (SEQ ID NO: 3), which is also referred to as PIE12-2. The PIE12-2 peptide has the same amino acid sequence as PIE12 (SEQ ID NO:1), except that a PEG4 moiety is inserted into the peptide backbone, between the glycine and lysine residues. The modification results in improved synthesis yields and reduced complexity of synthesis as it does not require an orthogonal lysine protecting group as for PIE12.

In one aspect, the present disclosure provides a composition comprising at least one D-peptide comprising SEQ ID NO:6 [HPCDYPEWQWLCELG-PEG$_4$-K], wherein the at least one D-peptide interacts with the N-trimer pocket of HIV gp41. In certain embodiments, the composition comprises at least two D-peptides comprising SEQ ID NO:6 [HPCDYPEWQWLCELG-(PEG$_4$)-K]. In certain embodiments, the composition comprises at least three D-peptides comprising SEQ ID NO:6 [HPCDYPEWQWLCELG-(PEG$_4$)-K]. In yet further embodiments, the composition comprises a plurality of D-peptides comprising SEQ ID NO:6 [HPCDYPEWQWLCELG-(PEG$_4$)-K]. In preferred embodiments, the D-peptide(s) may comprise an N-terminus blocked by an acetyl group (Ac) and a C-termini blocked by an amino group (NH$_2$). In certain embodiments, the D-peptide comprises or consists of Ac-HPCDYPEWQWLCELG-(PEG$_4$)-K—NH$_2$ (SEQ ID NO:3).

Multimers

In certain embodiments, the peptides disclosed herein can also be present as multimers, such as dimers or trimers. For example, when the multimer is a dimer, the dimer can be comprised of two identical peptides, or can be comprised of two different peptides. Alternatively, the multimer can also be a trimer. When the multimer is a trimer, the trimer can be comprised of two identical peptides and one different peptide, or three identical peptides, or three different peptides, each of which is distinct from each other.

Disclosed herein are multimers of the peptides which are described herein. In certain embodiments, the multimers disclosed herein can comprise at least one D-peptide (e.g., PIE12-2), which interacts with the N-trimer pocket of a viral transmembrane protein. The multimer can be a dimer, trimer, or higher order multiples such as a tetramer, but could also include multimers with 5, 6, 7, 8, 9, 10, 11, or 12 D-peptides. Thus, disclosed herein are compositions comprising multimers that include one or more D-peptides of the present disclosure (e.g., PIE12-2) In certain embodiments, the multimer is a homomultimer or heteromultimer. In certain embodiments, the composition comprises at least one dimer composed of two PIE12-2 D-peptides (SEQ ID NO:3). In other embodiments, the composition comprises at least one trimer composed of three PIE12-2 D-peptides (SEQ ID NO:3). In yet further embodiments, the composition comprises a plurality of homodimers or homotrimers of PIE12-2 D-peptides (SEQ ID NO:3). Heteromultimers comprising at least one PIE12-2 D-peptide (SEQ ID NO:3) may be composed with other PIE D-peptides as disclosed in US2014/0323392 and US2010/0184663, each of which is incorporated herein by reference in its entirety.

It is understood and herein contemplated that the disclosed D-peptides can be crosslinked to form multimers. In certain embodiments, the multimers may be crosslinked through the use of multimer scaffolds. An example of a crosslinker is polyethylene glycol (PEG) derivatized with N-hydroxysuccinimide (NHS)-ester (reacts with Lys) or maleimide (reacts with Cys). In other embodiments, crosslinkers can also contain two distinct linkage chemistries (e.g., NETS-ester on one end and maleimide on the other end). In particular embodiments, D-peptides may also be linked by direct disulfide bond formation between two Cys residues.

In certain embodiments, the multimer scaffold can be a trimeric scaffold comprising three NETS ester groups. In particular embodiments, the multimer scaffold may be a homotrimeric scaffold or a heterotrimeric scaffold comprising three NETS ester groups. Furthermore, in other embodiments, the multimer scaffold may be a tetrameric scaffold comprising three NETS ester groups and a fourth orthogonal group. In such embodiments, the multimer scaffold may be a heterotetrameric scaffold comprising three NHS ester groups and a fourth orthogonal group. Additionally, particular embodiments of the disclosed crosslinker and multimer scaffold can comprise a tris, di-lysine, benzene ring, phosphate, or peptide core. Other crosslinkers disclosed herein for use with the disclosed compositions comprise thiol-reactive groups, e.g., haloacetyls (e.g., iodoacetate), pyridyl disulfides (e.g., HPDP), and other thiols.

The D-peptides that are linked can be any of those disclosed herein, and the D-peptides can be identical to each other or can each be different. When a dimer is present, the N-termini of both of the D-peptides can be crosslinked to each other. Alternatively, the C-termini of the D-peptides can be crosslinked. Also, the N-terminus of one D-peptide and the C-terminus of the other D-peptide are crosslinked. When a trimer is present, the N-termini and C-termini of the D-peptides can be linked in any combination. For example, they can be linked in any of the following arrangements: N—N/C—C—peptide 1's N-terminus links to peptide 2's N-terminus; peptide 2's C-terminus links to peptide 3's C-terminus. Using this naming, there are 16 possible trimer lineages: X/Y where X and Y=N—N, N—C, C—N, or C—C. D-peptides can also be linked to a central scaffold by the N- or C-termini or an internal location or a combination of these. Thus, for example, it is contemplated herein that one or more D-peptides can be crosslinked at internal residues rather than a terminal crosslinking. It is further contemplated that in trimers an internal crosslinker can be used for one peptide pair (e.g., peptide 1 to peptide 2) and a terminal crosslinker (N- or C-termini) can be used for crosslinking peptide 2 to peptide 3.

As used herein, the naming scheme for multimers describes the way the peptides are connected. For example, C4C-PIE12-trimer means that three PIE12 peptides are connected via C- to C-terminal connections using a $PEG_4$ spacer. Note: The zero length spacers can be any of a variety of short crosslinkers (e.g., BS3, DSG, or DST). The structure of DSG is as follows:

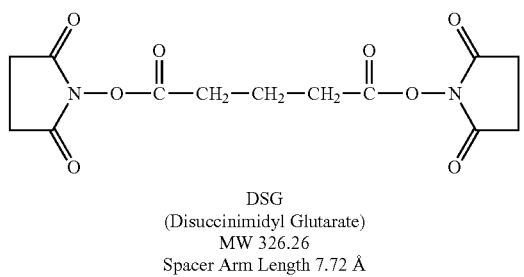 [SMILES: O=C(CCCC(=O)ON1C(=O)CCC1=O)ON1C(=O)CCC1=O]

DSG
(Disuccinimidyl Glutarate)
MW 326.26
Spacer Arm Length 7.72 Å

As used herein, the term "PIE12-trimer" is a generic term for a multimer that represents a number of molecules with slightly different chemical compositions in which three PIE12 monomers are linked together by various crosslinking strategies. In certain embodiments, one class of PIE12-trimer may be constructed by connecting monomers using PEG crosslinkers of various lengths without use of a central scaffold. In such embodiments, the trimers may be designated, for example, CxC-PIE12-trimer where "CxC" represents linkage of PIE12 monomers via a unique primary amine of a lysine side chain where the lysine residue is located at the C-terminus of the peptide monomer. In other embodiments, NxN-PIE12-trimers represent linkage by a lysine located at the N-terminus. The "x" in this context refers to the number of PEG units in the crosslinker connecting individual monomers. In particular embodiments, a central monomer containing two lysines may be used to make trimers of this type. An alternate name for trimers of this type is, for example, $C5C(PIE12)_3$ where the "3" subscript indicates a trimer.

A "PIE12-2 trimer" refers to three PIE12-2 monomer peptides (SEQ ID NO:3) that are linked together by various cross-linking strategies, for example using PEG crosslinkers of various lengths with or without use of a central scaffold.

As described herein, some embodiments of PIE12-2 trimers may be constructed using a central multimer scaffold containing a trivalent atom (i.e., nitrogen) at its core with three PEG linkers or "arms" of various length connecting PIE12-2 monomers into a trimer. In other embodiments, the central multimer scaffold may comprise the use of a tetravalent atom at the core of the multimer scaffold (i.e., carbon), with, for example, three PEG linkers of various lengths connecting individual PIE12-2 monomers.

In certain embodiments, potency-enhancing versions of PIE12-2 trimer may be assembled using a carbon core scaffold in which a potency-enhancing cargo moiety is attached to a PIE12-2 trimer utilizing the fourth arm of the tetravalent scaffold. In such embodiments, PEG units of various lengths (i.e., 12-132 PEG units) can be used to link various moieties to the 4th arm. One example of a PIE12-2 trimer is chol-$PEG_{32}$-PIE12-2 trimer, where "chol" is short for cholesterol and "$PEG_{32}$" refers to the total number of ethylene glycol repeats the 4th arm. In certain embodiments, the total number of ethylene glycol repeats ranges from 24-36. In certain embodiments, the total number of ethylene glycol repeats is 32. The fourth arm may be composed of a single PEG chain or a first PEG chain and a second PEG chains in series that link the potency enhancing cargo moiety to the multimer scaffold. In particular embodiments, the potency-enhancing cargo can be attached to the 4th arm PEG unit by various chemical reactivities.

The multimers disclosed herein can be made of any combination of peptides, including those disclosed in Table 1, or variants thereof, such that the multimers can inhibit viral entry into a cell. In certain embodiments, the multimers can comprise one PIE12-2 D-peptide, two PIE12-2 D-peptides, or three or more PIE12-2 D-peptides. In such embodiments, all of the peptides can be identical, or they can be composed of any combination of D-peptides, including those disclosed and those which are not specifically disclosed herein. In particular embodiments, at least one of the D-peptides can comprise the sequence Ac-HP-CDYPEWQWLCELG-($PEG_4$)-K—$NH_2$ (SEQ ID NO: 3).

Multimer Scaffold

As an alternate strategy for making multimers, a central multimeric scaffold can be used to attach one or more PIE D-peptides (e.g., PIE12 as set forth in SEQ ID NO: 1, PIE12-$PEG_4$ as set forth in SEQ ID NO: 2, or PIE12-2 as set forth in SEQ ID NO:3). For example, in one embodiment, a central multimeric scaffold is used to attach one or more PIE12-2 peptides. In particular embodiments, a multimeric scaffold as disclosed herein may comprise a central trifunctional crosslinker tris(succinimidyl) aminotriacetate, such as TSAT, which contains three N-hydroxysuccinimide (NHS) ester groups. In some embodiments, this geometry is referred to as "the claw", as the configuration resembles an eagle claw. Two examples of this strategy are (1) a short claw (which directly links TSAT to the peptides) and (2) a long claw (which uses an extended form of TSAT (LC-TSAT) that contains an additional six-atom spacer between TSAT and the peptides). Other spacer lengths or compositions (e.g., PEG) can also be used.

Below is a representation of LC-TSAT:

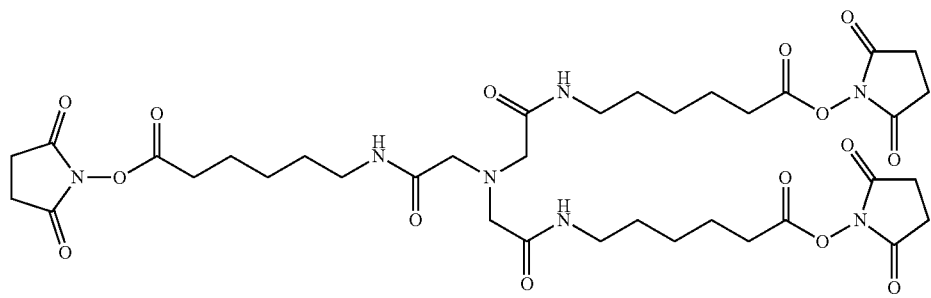 [SMILES: O=C(CN(CC(=O)NCCCCCC(=O)ON1C(=O)CCC1=O)CC(=O)NCCCCCC(=O)ON1C(=O)CCC1=O)NCCCCCC(=O)ON1C(=O)CCC1=O]

And the following is a representation of TSAT:

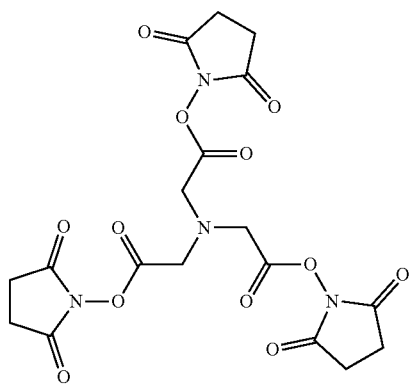 [SMILES: O=C(CN(CC(=O)ON1C(=O)CCC1=O)CC(=O)ON1C(=O)CCC1=O)ON1C(=O)CCC1=O]

"Over-engineering" future D-peptides means improving affinity even after reaching the potency limit. Such inhibitors do not show improved anti-viral potency in vitro, but have a reserve of binding energy (affinity) that acts as a "resistance capacitor" to defend against potential resistance mutations (i.e., resistance mutations that moderately affect binding affinity would have no effect on potency). This "resistance capacitor" property discourages the stepwise accumulation of multiple subtle mutations that combine to confer resistance. Individual mutations have no effect on inhibitor potency and do not confer a growth advantage in the presence of inhibitors. This "resistance capacitor" may be especially beneficial for trimeric D-peptide inhibitors, because resistance mutations simultaneously affect all three pockets. In certain embodiments, as a further defense against the development of resistance, the trimeric D-peptides disclosed herein can also be constructed by using three different D-peptide sequences, each with a distinct resistance profile. Such a heterotrimer would present a significant additional barrier to the development of resistance.

Heterotetramer

As disclosed herein, the PIE12-2 trimer is a potent inhibitor of HIV entry. The PIE12-2 trimer comprises further modifications over a predecessor compound CPT24 (cholesterol-$PEG_{24}$-PIE12 trimer) that allow for PIE12-2 trimer to: 1) be synthesized more easily and in higher yield; 2) to possess enhanced pharmacokinetic properties (e.g., by reducing renal filtration since it is smaller than the glomerular filtration cutoff molecular weight); 3) to allow for local concentration on the cell surfaces where HIV entry takes place; and 4) improve potency by overcoming the kinetic potency limit. In particular embodiments, to produce PIE12-2 trimers with some or all of these improved properties, a custom-designed heterotetrameric PEG scaffold can be employed. This scaffold typically has three arms with one type of reactive group (e.g., NHS ester) for attachment of the PIE D-peptide. A fourth group, typically with a longer PEG arm, has a reactive group orthogonal to the other three arms (e.g., maleimide if the three arms have NHS esters). This modular heterotetramer scaffold design allows straightforward modification of any of the PEG arm lengths and significantly simplifies synthesis of trimeric PIE D-peptides with appended potency-enhancing cargoes. Below is an example of a heterotetrameric PEG scaffold for a PIE12 trimer (see, US2014/0323392). This scaffold is based on a 3-{2-Amino-3-(2-carboxyethoxy)-2-[(2-carboxyethoxy) methyl]propoxy}propionic acid scaffold, which is also used by the CPT24 compound disclosed herein.

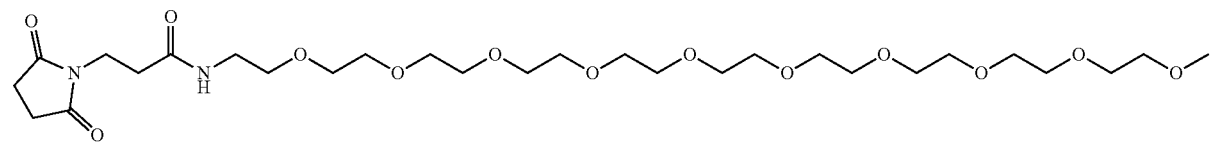

-continued

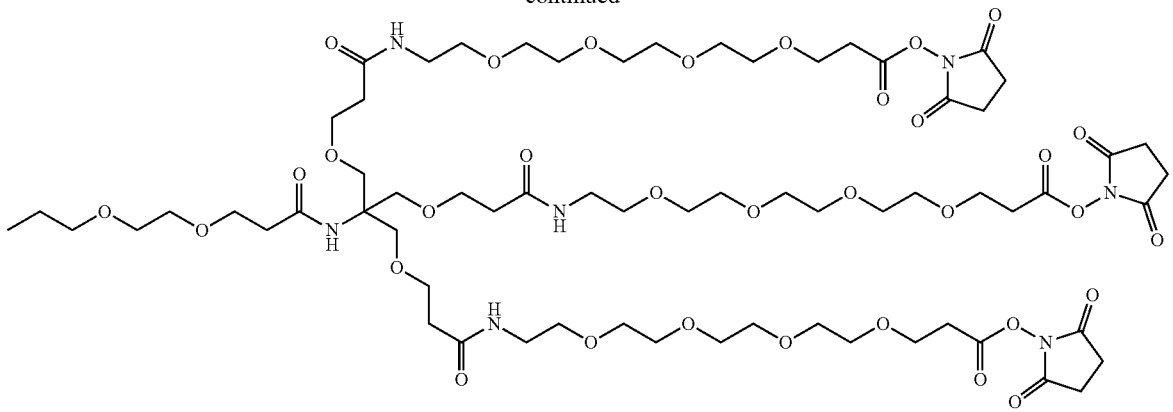

In certain embodiments, the presently disclosed compositions comprise a multimer scaffold, such as a heterotetramer scaffold, that can be modified to comprise a potency-enhancing cargo molecule. As used herein, a potency-enhancing cargo molecule is a cargo molecule that enhances the potency of the compositions disclosed herein. In some embodiments, a potency-enhancing cargo molecule comprises a cargo molecule that has pharmacokinetic-enhancing properties. In other embodiments, a potency-enhancing cargo comprises a cargo molecule that has membrane-localizing properties. In particular embodiments, the potency-enhancing cargo molecule may comprise a pharmacokinetic-enhancing cargo molecule including any group that will reduce clearance of the attached peptide. For example, disclosed herein are compositions comprising a multimer scaffold with a potency-enhancing cargo molecule, wherein the potency-enhancing cargo molecule is a sterol (e.g., cholesterol) or analog thereof (e.g., thiocholesterol), albumin, polyethylene glycol (e.g., linear or branched), a sugar, maltose binding protein, serum albumin, ubiquitin, streptavidin, immunoglobulin domains, keyhole limpet hemacyanin, sperm whale myoovalbumin, bovine pancreatic trypsin inhibitor, green fluorescent protein, gold particle, magnetic particle, agarose bead, lactose bead, an alkane chain (e.g., C8, C16, C18 alkane chain), or fatty acid (e.g., C8 fatty acid, C16 fatty acid, C18 fatty acid, palmitate). In other embodiments, the potency-enhancing cargo molecule can be the linking of multiple multimers, such as the linking of multiple trimers (to increase molecular weight and reduce renal filtration). In certain embodiments, cholesteryl chloroformate precursor is linked to the multimer scaffold. Thus, for example, disclosed herein are compositions comprising one or more D-peptide PIE12-2 peptides, a multimer scaffold, and a potency-enhancing cargo molecule, wherein the potency-enhancing cargo molecule is cholesterol or an analog thereof.

In certain embodiments, the compositions disclosed herein include a PIE12-2 multimer (e.g., trimer) with a multimer scaffold based on 4-Amino-4-(2-carboxyethyl)heptanedioic acid as shown:

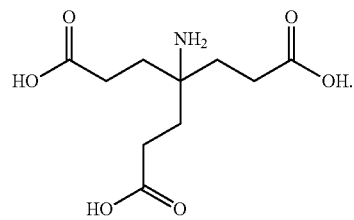 [SMILES: NC(CCC(=O)O)(CCC(=O)O)CCC(=O)O]

Figure 5:
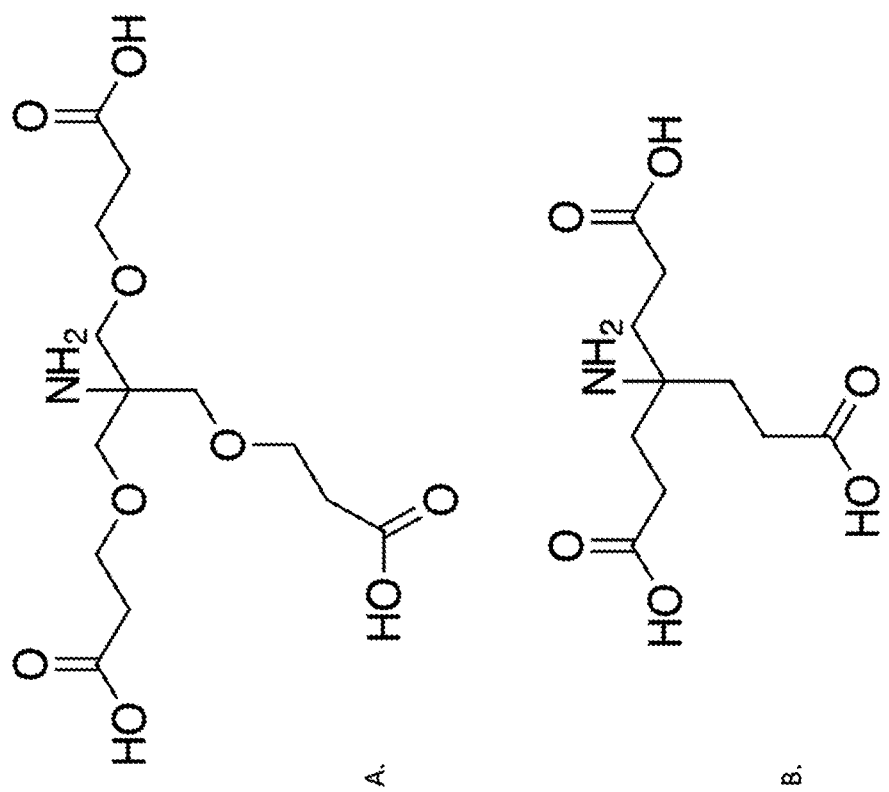
FIGS. 5A-B depict the multimer scaffolds used for CPT24 and CPT31. (A) CPT24 uses a 3-{2-Amino-3-(2-carboxy-ethoxy)-2-[(2-carboxyethoxy)methyl]propoxy}propionic acid scaffold. (B) CPT31 uses a 4-Amino-4-(2-carboxy-ethyl)heptanedioic acid scaffold.

The 4-Amino-4-(2-carboxyethyl)heptanedioic acid multimer scaffold is used by the CPT31 compound disclosed herein. The 4-Amino-4-(2-carboxyethyl)heptanedioic acid multimer scaffold and 3-{2-Amino-3-(2-carboxyethoxy)-2-[(2-carboxyethoxy)methyl]propoxy}propionic acid multimer scaffold both comprise a tetrahedral carbon core (FIG. 5). However, the use of 4-Amino-4-(2-carboxyethyl)heptanedioic acid multimer scaffold results in large scale synthesis at a lower cost.

In certain embodiments, the PIE12-2 multimers disclosed herein comprise each PIE12-2 D-peptide linked to an arm of a multimer scaffold comprising three arms via an amide bond between the epsilon amino group of the C-terminal D-lysine of the PIE12-2 D-peptide and a carboxyl group of the arm of the multimer scaffold, wherein the multimer scaffold is based on 4-Amino-4-(2-carboxyethyl)heptanedioic acid.

In particular embodiments, the compositions disclosed herein include at least one PIE12-2 trimer with a pharmacokinetic-enhancing cargo having the following structure:

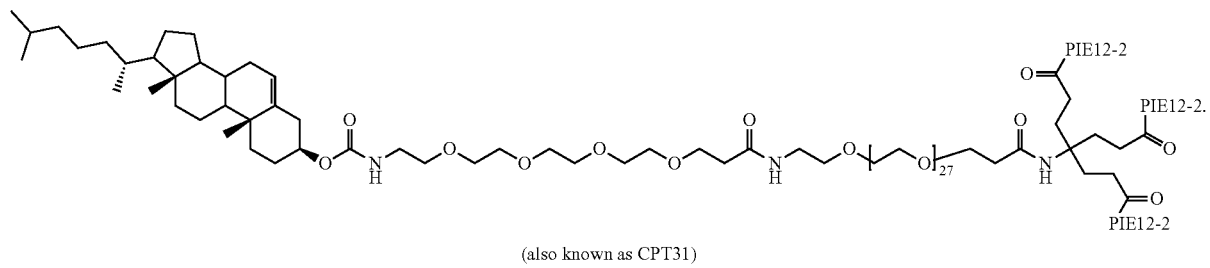

(also known as CPT31)

CPT31 has a monoisotropic molecular mass of 9029.37 Da, with a chemical formula of $C_{423}H_{637}N_{75}O_{129}S_6$.

Figure 4:
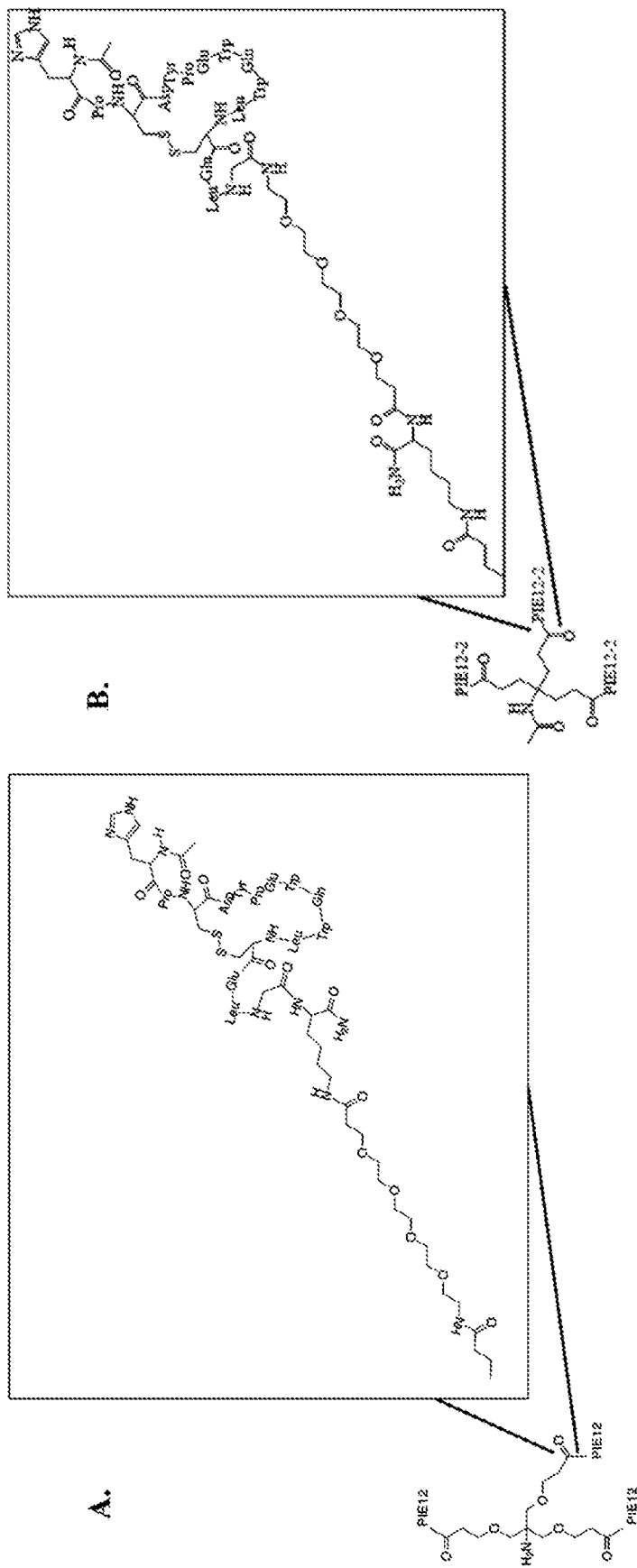
FIGS. 4A-B depict the attachment of the PIE12 peptide to the multimer scaffold arms for CPT24 in panel A and the attachment of the PIE12-2 peptide to the multimer scaffold arms for CPT31 in panel B. (A) An amide bond is formed between the terminal amino group of the PEG4 and the carboxy group of the scaffold peptide arm. (B) An amide bond is formed between the epsilon amino group of D-lysine side chain and the carboxyl group of the scaffold peptide arm.

As noted earlier, the peptide sequence of PIE12-2 is a variant of PIE12. The PIE12 trimer CPT24 (thiocholesterol-PEG24-PIE12 trimer) utilized a PEG4 spacer attached to each PIE12 (SEQ ID NO:1) monomer via an amide bond at the epsilon amino group of the C-terminal D-lysine side to yield "PIE12-PEG4" (SEQ ID NO:2). The attachment of PIE12-PEG4 is achieved by condensation between the terminal amino group of the PEG4 and the carboxyl group of the scaffold, producing an amide bond (FIG. 4A). The synthesis of PIE12-PEG4 is more complex synthetically. As a result, yield of the peptide is lower, and synthesis requires non-standard amino acid side chain protection at the C-terminal D-lysine. PIE12-2 was created by moving the PEG4 linker into the peptide backbone between the C-terminal D-lysine and the adjacent glycine. The attachment of PIE12-2 to the scaffold is thus achieved by an amide bond between the epsilon amino group of the C-terminal D-lysine and the carboxyl group of the scaffold by condensation (FIG. 4B), avoiding the need for an orthogonal Lys protecting group.

In other embodiments, PEG linkers comprising 2, 3, 5, 6, 7, or 8 ethylene glycol repeats can be inserted into the PIE12-2 arms between the glycine residue and C-terminal lysine residue of the PIE12-2 peptides.

In certain embodiments, the PIE12-2 multimer disclosed herein comprises PIE12-2 D-peptides and linkage to the multimer scaffold as shown in FIG. 4B.

Also disclosed herein are PEG linkers. In certain embodiments, the PEGylation that generates a multimer can result in a PEG linker of varying lengths. In particular embodiments, the use of such PEG linkers provides space between the potency-enhancing cargo molecule (e.g., cholesterol) and the D-peptide pocket-specific inhibitors of entry (e.g., PIE12-2 monomer, PIE12-2 multimer). It is understood and herein contemplated that the length of the PEG linker can improve $IC_{50}$ and the half-life of the composition. However, too bulky a linker can also have detrimental effects. Thus, disclosed herein are compositions wherein the PEG linker is a linker between the potency-enhancing cargo molecule and D-peptide pocket-specific inhibitors of entry comprising 12-132, or preferably 24-48 ethylene glycol repeats. In certain embodiments, the PEG linker may have 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 96, 97, 98, 99, 100, 101, 102, 103 104, 105, 106, 107, 108, 109, 110, 111, 112, 113, 114, 115, 116, 117, 118, 119, 120, 121, 122, 123, 124, 125, 126, 127, 128, 129, 130, 131, or 132 ethylene glycol repeats in total. The PEG linker may be composed of a single PEG chain or a first PEG chain and a second PEG chain linked in series. Various chemistries that are known in the art may be used to conjugate the potency enhancing cargo molecule molecule (e.g., cholesterol) to the PEG chain. For example, cholesterol may be conjugated to the PEG chain via carbamate, formed via halide formate cholesterol (e.g., cholesteryl chloroformate) reacting with an amine. In another example, cholesterol may be conjugated to the PEG chain via amide, formed by condensation between a carboxylic acid cholesterol and amine. In another example, cholesterol may be conjugated to the PEG chain via amide, formed by a cholesterol-NHS or any other active ester (such as PFP). In another example, cholesterol may be conjugated to the PEG chain via amide, formed by reaction of ketone with an amine (isourea). In another example, cholesterol may be conjugated to the PEG chain via a thioether bond, formed by reaction of thiol (such as thiocholesterol) with a maleimide ester. In another example, cholesterol may be conjugated to the PEG chain via an ether bond, for example via dehydration reaction with a terminal hydroxyl on a cholesterol-PEG and the PEG linker of the fourth arm of the multimer scaffold. In yet another example, cholesterol may be conjugated to the PEG chain via click chemistry, for example Huisgen 1,3-diploar cycloaddition between azide and alkyne. In certain embodiments, addition of the cholesterol moiety to the fourth arm of the multimer scaffold via the PEG linker does not create stereoisomers.

Figure 3:
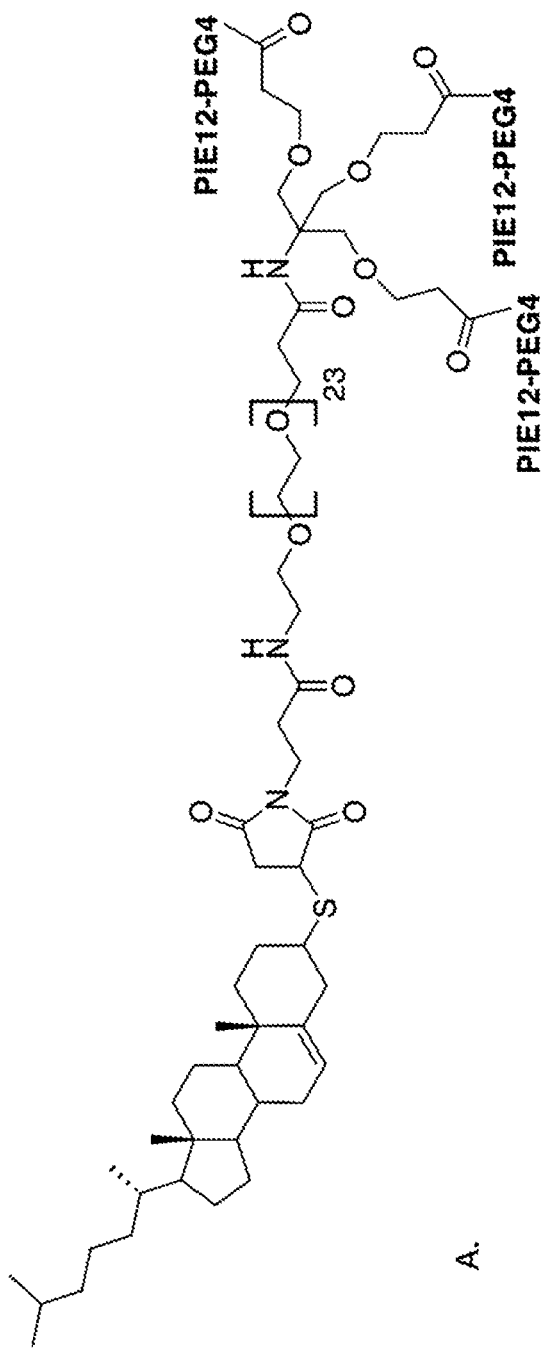
FIGS. 3A-B depict the structure of CPT24 (cholesterol-PEG24-PIE12 trimer) in panel A and the structure of CPT31 (cholesteryl-PEG32-PIE12-2 trimer) in panel B.
Figure 3:
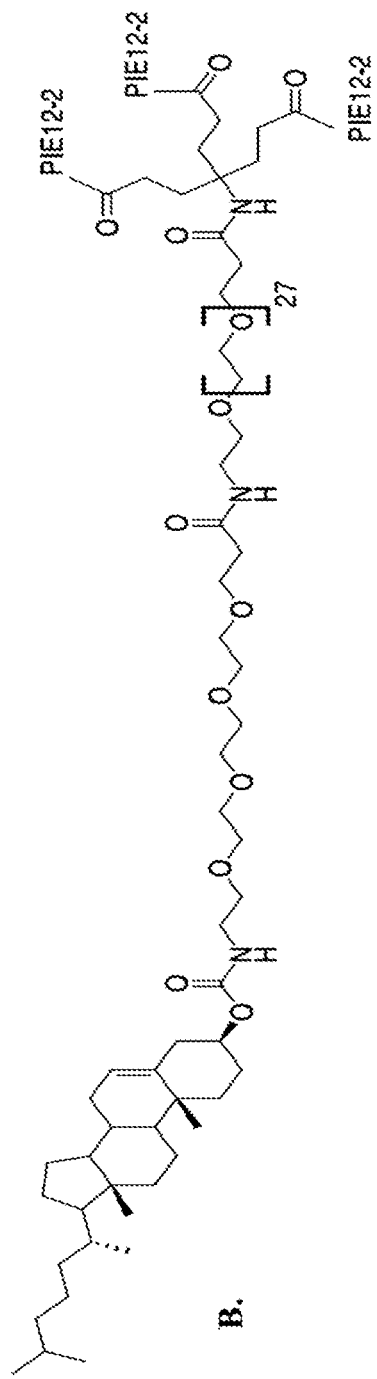

The CPT24 compound as previously described (see, US2014/0323392) uses a continuous PEG24 chain to join thiocholesterol to the PIE12 trimer scaffold (FIG. 3A). As disclosed herein, exemplary PIE12-2 trimers use two PEG chains in series for the fourth arm linking the potency enhancing cargo molecule to the multimer scaffold (FIG. 3B). This change significantly improves the ability to purify the peptide trimer prior to addition of cholesterol, resulting in improved yields and purity. In certain embodiments, a PIE12-2 trimer comprises a fourth arm linking a potency enhancing cargo molecule (e.g., cholesterol moiety) via a first and a second polyethylene glycol (PEG) chains linked in series to the multimer scaffold, wherein the total number of ethylene glycol repeats in the fourth arm from the first and second PEG chains ranges from 12 to 132 or 24 to 48. In certain embodiments, the total number of ethylene glycol repeats in the fourth arm from the first and second PEG chains is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 96, 97, 98, 99, 100, 101, 102, 103 104, 105, 106, 107, 108, 109, 110, 111, 112, 113, 114, 115, 116, 117, 118, 119, 120, 121, 122, 123, 124, 125, 126, 127, 128, 129, 130, 131, or 132. Accordingly, for a total of 32 ethylene glycol repeats, disclosed herein are a first PEG chain comprising 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 ethylene glycol repeats and a second PEG chain comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 ethylene glycol repeats, respectively. In a specific embodiment, the first PEG chain comprises 28 ethylene glycol repeats and the second PEG chain comprises 4 ethylene glycol repeats. Unless otherwise indicated, it is understood that a PEG chain comprising "n" ethylene glycol repeats is referred to as $PEG_n$. For example, $PEG_4$ refers to a PEG chain having 4 ethylene glycol repeat units.

Previous PIE trimer scaffolds were linked to thiocholesterol via fourth PEG arm using a maleimide ester. Maleimide esters are problematic due to the ability of the thiocholesterol to react at either C3 or C4 of the maleimide ring, creating stereoisomers that are very difficult to separate. Furthermore, maleimide esters can undergo a base-dependent ring opening to yield a linear 5-carbon chain. In contrast, exemplary PIE12-2 trimer comprising a multimer scaffold (e.g., 4-Amino-4-(2-carboxyethyl)heptanedioic acid) utilize a cholesteryl chloroformate precursor that reacts with the terminal amino group of the fourth arm PEG chain to yield a cholesteryl carbamate linkage (FIG. 3B). This linkage does not create a stereocenter, and does not undergo degradation to yield an undesired by-product. In certain embodiments of the PIE12-2 trimers utilizing a multimer scaffold, the presence of the cholesterol moiety on the fourth arm of the multimer scaffold does not create stereoisomers.

In certain embodiments, the first PEG chain is linked to the multimer scaffold via an amide bond. In certain embodiments, the second PEG chain is linked to the first PEG chain via an amide bond. In certain embodiments, the first or second PEG chain, or both, comprises an NHS ester group for creating the amide bond linkage. The cholesterol moiety may be linked to the second PEG chain via a carbamate linkage.

In certain embodiments, the first PEG chain is linked to the PIE12-2 multimer scaffold prior to linking of the cholesterol moiety and second PEG chain. In further embodiments, wherein after linking the first PEG chain to the multimer scaffold, the composition is purified prior to linking of the cholesterol moiety and second PEG chain.

Thus, it is understood that the disclosed compositions can comprise the culmination of all the features disclosed herein such as one or more D-peptides, multimer scaffolding, potency-enhancing cargo, and modification of the flanking regions of D-peptides, and PEG linkers. Accordingly, disclosed herein are compositions comprising one or more D-peptides and a potency-enhancing cargo, wherein the one or more D-peptides are linked by a multimer scaffold, wherein the multimer scaffold is linked to the D-peptides, optionally via a PEG linker, and wherein the potency-enhancing cargo is linked to the multimer scaffold via a PEG linker.

The multimer scaffold as disclosed herein may be use for a multimer scaffold-based design method for multimeric D-peptide drug optimization (both peptide geometry and localization to the site of action via conjugated localizing cargoes). In certain embodiments, multimer scaffold-based design allows for alterations in the scaffold to accommodate a variety of cargoes and chemistries (e.g., "click" chemistry), as well as rapid optimization of PEG arm lengths. For example, for viruses that undergo membrane fusion within the endosome, such as HIV and Ebola, the multimer scaffold-based strategies disclosed herein could be employed to identify and attach an endosome-targeting moiety to localize an inhibitor to the site of virus entry and increase inhibitor potency. Additionally, particular embodiments of the multimer scaffold-based strategy as disclosed herein may allow for the identification of, and conjugation to a variety of potency-enhancing cargoes to modulate pharmacokinetic properties (e.g., large branched PEGs, albumin, or albumin-binding peptides) and membrane localization.

Avidity of Multimers

Disclosed herein are compositions comprising a PIE12-2 multimer as disclosed herein and an N-trimer molecule, wherein the multimer, when associated with the N-trimer molecule, has an increased affinity for the N-trimer molecule, when compared with the affinity of a single peptide, or control peptide, for the N-trimer molecule. The single peptide, or control peptide, can be identical to one of the components of the multimer, or the single peptide can be a different peptide which is not contained in the multimer.

The multimer can exhibit about a 2-fold, 3-fold, 4-fold, 5-fold, 10-fold, 20-fold, 25-fold, 30-fold, 40-fold, 50-fold, 100-fold, 200-fold, 300-fold, 400-fold, 500-fold, 1000-fold, 2000-fold, 3000-fold, 4000-fold, 5000-fold, or 10,000-fold increase in affinity for the N-trimer when compared with the affinity of one of the components of the multimer alone.

The multimer can have any of the characteristics or properties that are disclosed herein. Any of the multimers disclosed herein are capable of having avidity as described herein, and any of them can be used with the methods disclosed herein for increasing inhibition of viral entry.

Pharmaceutical Compositions

The PIE12-2 peptide and multimers thereof (e.g., CPT31) disclosed herein (alternatively referred to as compositions) can also be administered in vivo in a pharmaceutically acceptable carrier. By "pharmaceutically acceptable" is meant a material that is not biologically or otherwise undesirable, i.e., the material may be administered to a subject, along with the peptide disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, by subcutaneous injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disease, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system (i.e., depot) such that a constant dosage is maintained. See, e.g., U.S. Pat. No. 3,610,795, which is incorporated by reference herein.

The compositions, including PIE12-2 peptides and multimers (e.g., CPT31) thereof, can be used therapeutically in combination with a pharmaceutically acceptable carrier. Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution may be from about 5 to about 8, and alternatively from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed peptides and multimers thereof can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable. Additionally, it is contemplated herein that compositions designed for oral administration can further comprise gut permeabilizing agents.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

Effective dosages and schedules for administering the compositions disclosed herein, including the PIE12-2 peptides and multimers thereof (e.g., CPT31) disclosed herein, may be determined empirically, and making such determinations is within the skill in the art. The dosage ranges for the administration of the compositions are those large enough to produce the desired effect in which the symptoms/disorder is affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products, particularly for D-peptides. Examples of such guidance can be found throughout the literature. For example, the peptide FUZEON®, which has been FDA approved, can act as a guide for the dosages required for the peptides disclosed herein. In one embodiment, the typical daily dosage of the peptides or multimers thereof used alone might range from about 1 µg/kg to up to 100 mg/kg of body weight or more per day, depending on the factors mentioned above. Furthermore, the peptides disclosed herein can be administered several times daily, daily, weekly, monthly, or yearly, depending on the condition of the subject, other modes of therapy, etc. One of skill in the art could readily ascertain an appropriate dosing schedule.

Following administration of a disclosed composition, such as a peptide for treating, inhibiting, or preventing a viral infection, such as HIV, the efficacy of the peptide or multimer thereof can be assessed in various ways well known to the skilled practitioner. For instance, one of ordinary skill in the art will understand that a composition, such as a D-peptide, disclosed herein is efficacious in treating or inhibiting a viral infection in a subject by observing that the composition inhibits viral entry. Efficacy of the administration of the disclosed composition may also be determined by measuring the number of uninfected cells in the infected subject. A treatment that inhibits an initial or further decrease in uninfected cells in a subject or patient, or that result in an increase in the number of uninfected cells in, for example, the HIV-positive subject, is an efficacious treatment. The efficacy of a prophylactic treatment (i.e., preventative agent) can also be evaluated using indirect measures of infection, such as CD4+ cell counts, levels of anti-virus antibodies, and PCR to detect viral RNA levels.

The compositions that inhibit HIV entry, i.e., microbicides, disclosed herein may be administered prophylactically to patients or subjects who are at risk for being exposed to HIV or who have been newly exposed to HIV. In subjects who have been newly exposed to a virus such as HIV but who have not yet displayed the presence of the virus (as measured by PCR or other assays for detecting the virus) in blood or other body fluid, treatment with a peptide or multimer thereof includes administering a therapeutically effective dose of a composition, a peptide or multimer as described herein to the subject such that the ability of the virus to infect cells is partially or completely inhibited.

The disclosed peptides can be used to inhibit HIV entry by inhibiting HIV transmembrane protein. The term "inhibit HIV transmembrane protein" refers to a reduction in the number of HIV particles that are capable of entering a host cell. It can mean complete inhibition, in other words no viral particles are capable of entering a cell, or it can mean a partial inhibition, meaning that in a given system there is a reduction in the number of HIV particles capable of entering a cell when compared with a non-treated system, or a control. There can be a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38, 39, 40, 41, 42, 43, 44, 45, 46, 47, 48, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% reduction in the number of HIV particles that are capable of entering a cell, or any amount greater, less, or in between these amounts. Additionally, to "inhibit HIV entry" means to reduce fusion and entry of HIV virions into a host cell.

Methods of Making the Compositions

The compositions disclosed herein and the compositions necessary to perform the disclosed methods can be made using any method known to those of skill in the art for that particular reagent or compound unless otherwise specifically noted.

The peptides disclosed herein can be linked, for example, by disulfide crosslinks. For example, the D-peptides disclosed herein have two Cys residues connected by a disulfide bond, which circularizes the peptide and creates a more compact and structured peptide. This disulfide is known to have enhanced antiviral properties. There are many alternative methods for circularizing peptides known to those of skill in the art. For example, a peptide can be circularized using lactam or other chemical bridges, PEG or other chemical crosslinkers, peptide ligation, or diselenide bonds (between selenocysteines).

Two or more peptides or polypeptides can also be linked together by protein chemistry techniques. For example, peptides or polypeptides can be chemically synthesized using currently available laboratory equipment using either FMOC (9fluorenylmethyloxycarbonyl) or Boc (tert butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W. H. Freeman and Co., N.Y. (1992); Bodansky M and Trost B., Ed. (1993) Principles of Peptide Synthesis. SpringerVerlag Inc., N.Y. (which is herein incorporated by reference at least for material related to peptide synthesis). Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776779 (1994)). The first step is the chemoselective reaction of an unprotected synthetic peptidethioester with another unprotected peptide segment containing an aminoterminal Cys residue to give a thioester linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; ClarkLewis I et al., J. Biol. Chem., 269:16075 (1994); ClarkLewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (nonpeptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, N.Y., pp. 257267 (1992)).

Mirror-image phage display can be used to discover D-peptides that bind to the N-trimer pocket and inhibit HIV-1 entry with modest potency. For example, in using mirror-image phage display to screen for D-peptides, a first D-peptide can be synthesized from the first L-peptide from a HIV glycoprotein. The first L-peptide can be a naturally occurring L-peptide or can be a chimera of designed peptide sequences and natural peptide sequences. The methods can further comprise screening for a second L-peptide that specifically binds to the first D-peptide; then, a second D-peptide that is the mirror image of the second L-peptide can be synthesized. In one aspect of the D-peptide screening methods described herein, an N-trimer target can first be synthesized with D-amino acids, creating the mirror image of the natural L-N-trimer target. The D-N-trimer target can be used in standard peptide-based screens such as phage display, ribosome display, and/or CIS display to identify L-peptides that bind to the D-N-trimer. The identified L-peptides can then be synthesized with D-amino acids. By the law of symmetry, the resulting D-peptides bind the natural L-N-trimer, and will thus target the N-trimer region of the HIV prehairpin intermediate, thereby treating or inhibiting HIV infection. This screening method is also described in Schumacher, et al., Identification of D-peptide ligands through mirror-image phage display, Science, 1996 Mar. 29; 271(5257):1854-7, which is hereby incorporated in its entirety by this reference.

The present disclosure also provides methods of synthesizing a trimeric D-peptide-cholesterol conjugate of the following structure,

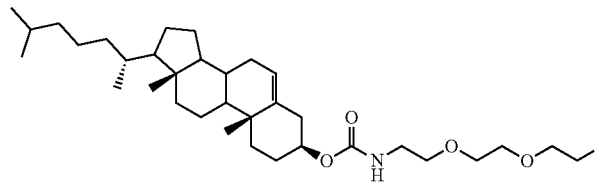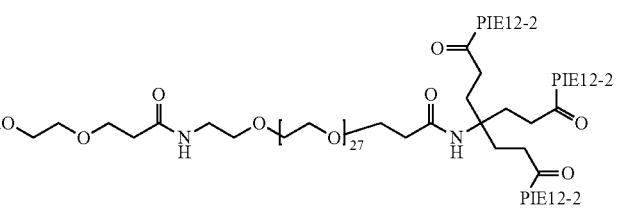

Figure 6:
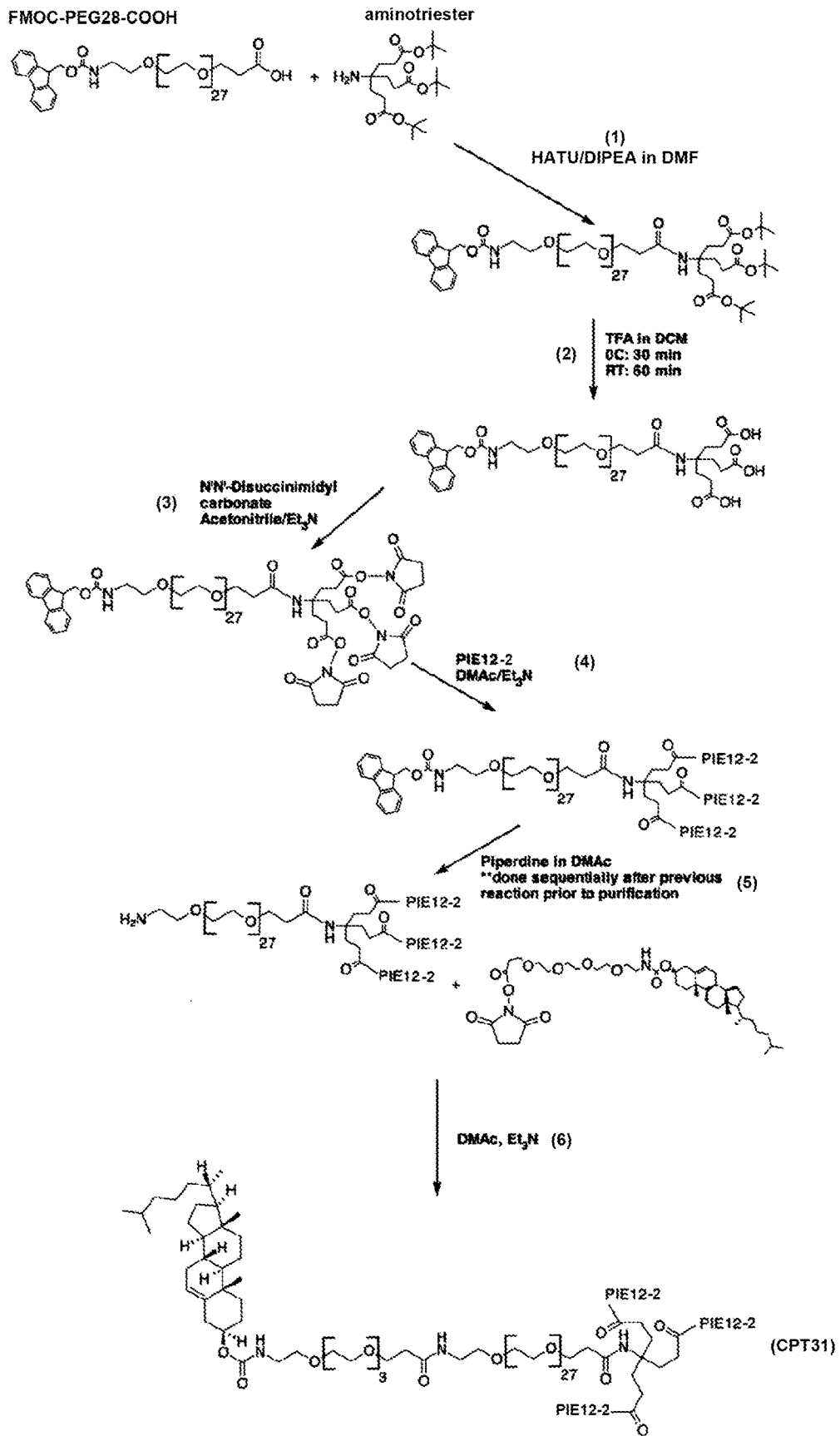
FIG. 6 depicts an overview of an exemplary synthesis method for CPT31. In step (1), FMOC-PEG28-COOH is conjugated to an aminotriester multimer scaffold using (1-[Bis(dimethylamino)methylene]-1H-1,2,3-triazolo[4,5-b]pyridinium 3-oxid hexafluorophosphate) (HATU), to yield FMOC-PEG28-triester. In step (2), the FMOC-PEG28-triester is completely deprotected to yield FMOC-PEG28-triacid. In step (3), the FMOC-PEG28-triacid is activated using N'N'-Disuccinimidyl carbonate. In step (4), three

(also known as CPT31)

wherein the method comprises the steps set forth in FIG. 6. Further details of the synthesis methods are also set forth in the Examples described herein.

Methods of Inhibiting Viral Entry

Disclosed herein are methods for inhibition of transmission or entry of HIV into a host cell, or inhibiting HIV entry, comprising exposing HIV to compositions, PIE12-2 peptides or multimers thereof (e.g., CPT31) as disclosed herein, and thereby inhibiting transmission of the HIV to the host cell. In certain embodiments, the host cell is human. Also disclosed herein are methods of treating HIV infection in a subject comprising administering to the subject an effective amount of the compositions, PIE12-2 peptides or multimers (e.g., CPT31) as disclosed herein, thereby treating HIV infection. Examples of HIV viruses include HIV-1 and HIV-2. The peptides or multimers can be in a pharmaceutical composition. Also disclosed are methods of administering a pharmaceutical composition described herein.

The methods disclosed herein can be used in conjunction with other viral therapies or antiviral agents. One of more of these antiviral agents can be used, and they can be administered before, during, or after treatment with the compositions disclosed herein. For example, in ongoing therapy, the subject can be administered the compositions comprised herein simultaneously with other treatments, meaning they can be administered about 48 hours, 24 hours, 12 hours, 8 hours, 4 hours, 2 hours, 1 hour, 30 minutes, 20 minutes, 10 minutes, 5 minutes, or one minute before treatment with the disclosed compositions. Other methods of treatment can also be administered before treatment with the compositions disclosed herein. By "before treatment" is meant that another form of treatment was given and then stopped before the current therapy was administered, or could be given immediately before, then administered again afterwards. In this case, the other methods of antiviral therapy can be administered years, months, weeks, days, hours, or minutes in advance. Other methods of treatment can also be administered after treatment with the compositions disclosed herein. By "after treatment" is meant that another form of treatment is administered after the current therapy was administered, or could be given before, then administered again afterwards. This additional antiviral treatment could be given years, months, weeks, days, hours, or minutes after the current therapy is given.

The further antiviral agent or agents can be selected from the group consisting of a viral replication inhibitor, a viral protease inhibitor, a viral reverse transcriptase inhibitor, a viral entry inhibitor, a viral integrase inhibitor, a viral Rev inhibitor, a viral Tat inhibitor, a viral Nef inhibitor, a viral Vpr inhibitor, a viral Vpu inhibitor, and a viral Vif inhibitor.

Further examples of antiviral compounds include, but are not limited to, amantadine, rimantadine, zanamavir and oseltamavir (Tamiflu) for the treatment of flu and its associated symptoms. Antiviral compounds useful in the treatment of HIV include Combivir® (lamivudine-zidovudine), CRIXIVAN® (indinavir), EMTRIVA® (emtricitabine), EPIVIR® (lamivudine), FORTOVASE® (saquinavir-sg), HIVID® (zalcitabine), INVIRASE® (saquinavir-hg), KALETRA® (lopinavir-ritonavir), LEXIVA™ (fosamprenavir), NORVIR® (ritonavir), RITROVIR® (zidovudine) SUSTIVA® (efavirenz), VIDEX EC® (didanosine), VIDEX® (didanosine), VIRACEPT® (nelfinavir) VIRAIVIUNE® (nevirapine), ZERIT® (stavudine), ZIAGEN® (abacavir), FUZEON® (enfuvirtide) RESCRIPTOR® (delavirdine), REYATAZ® (atazanavir), TRIZIVIR® (abacavir-lamivudine-zidovudine) VIREAD® (tenofovir disoproxil fumarate) ISENTRESS® (raltegravir), SELZENTRY® (maraviroc), and AGENERASE® (amprenavir).

EXAMPLES

Example 1

Materials and Methods

Synthesis of PIE12-trimer and PIE12-trimer Conjugates

PIE12 (Ac-HPCDYPEWQWLCELGK) was synthesized by RS Synthesis (Louisville, Ky.). PIE12-trimer and maleimide-PEG24-PIE12-trimer were synthesized as previously described (see, Francis et al., 2012, Bioconjug. Chem. 23:1252-1258, U.S. Patent Publication 2014/0323392, each of which is incorporated herein by reference in its entirety). PIE12-trimers conjugated to cholesterol (cholesterol-PIE12-trimer with PEG24 fourth-arm spacer, CPT24), C8, C16, or C18 were synthesized in a similar manner by reacting maleimide-PEG24-PIE12-trimer (3 mM) with 4.5 mM thio-cholesterol (Sigma Aldrich #136115), 1-octanethiol (4.5 mM, Sigma Aldrich #471836), 1-hexadecanethiol (4.5 mM, Sigma Aldrich #52270), or 1-octadecanethiol (4.5 mM, Sigma Aldrich #01858), respectively, in dimethylacetamide (DMAC) with Et$_3$N (200 mM) for 60 min at RT, then purified by RP-HPLC. Palmitate-conjugated PIE12-trimer was synthesized by first reacting maleimide-PEG24-PIE12- trimer (3 mM) with D-cysteine (4.5 mM) in DMAC with Et$_3$N (200 mM) for 60 min at RT, then purified by RP-HPLC. The resulting product, Cys-PEG24-PIE12-trimer (2 mM), was then reacted with palmitic acid NHS ester (5 mM, Sigma Aldrich #P1162) in DMAC with Et$_3$N (500 mM) for 45 min at RT, then purified by RP-HPLC. 40 kD PEG-PEG24-PIE12 trimer (PEG40-PIE12-trimer) was synthesized by reacting Cys-PEG24-PIE12-trimer (2 mM) with NHS-PEG4-NHS (ChemPep #281903) followed sequentially by 2.5 mM 40 kDa Y branched PEG-amine (JenKem, A0010), then purified by RP-HPLC.

Synthesis of FMOC-PEG28-triNHS

FMOC-PEG28-COOH (Polypure, #15137-2790, 10 mmoles), aminotriester (Frontier Scientific, #NTN1963, 11 mmoles) and 1-hydroxy-7-azabenzotriazole (Aapptec, CXZ012, 9.8 mmoles) were suspended in 20 ml dichloromethane. This solution was placed on ice and stirred for 20 minutes prior to the addition of N,N'-dicyclohexylcarbodiimide (Sigma Aldrich, D80002, 9.8 mmoles). This reaction was stirred on ice for 30 minutes, then warmed to room temperature with stirring for 12 h before purification by flash chromatography (Biotage Zip column) using a gradient of ethanol in dichloromethane. The resulting product was then dried by rotary evaporation to yield a viscous amber oil. This was then dissolved in dichloromethane (5 ml/g) and placed on ice with stirring. To this, 20 equivalents of trifluoroacetic acid were added dropwise, and the reaction was stirred for 30 min before warming to room temperature. After 3 h, the reaction was purified by reverse-phase chromatography (Biotage C18 flash column) using a gradient of water in acetonitrile. The resulting product was lyophilized, then dried repeatedly from toluene. The resulting FMOC-PEG28-triacid was suspended in acetonitrile to a concentration of 500 mM, to which N,N'-disuccinimidyl carbonate (Sigma Aldrich, #225827) was added to 1650 mM, followed by triethylamine to 400 mM. The reaction was stirred for 45 min at 45° C., then purified using flash chromatography (Biotage ZIP column) using a gradient of ethanol in dichloromethane.

Synthesis of Cholesteryl-PEG4-NHS

FMOC-PEG4-COOH (ChemPep, #280109) was suspended in dichloromethane to a concentration of 200 mM. To this, 5 equivalents of N,N-Diisopropylethylamine (DIPEA, Sigma Aldrich) was added, then the solution was added to 2-chlorotrityl chloride resin (Aapptec, #RTZ001). The mixture was agitated with argon gas for 2 h, then washed with dichloromethane (3×) followed by dichloromethane:methanol:DIPEA (17:2:1), then dichloromethane (3×). To this, a solution of dimethyl formamide:dichloromethane:piperdine (1:1:1) was added to remove the FMOC protecting group, and the reaction was agitated with argon gas for 40 min before being washed with dimethyl formamide, then dimethylformamide:dichloromethane (1:1), then dichloromethane. To the resin was added 2 equivalents of cholesteryl chloroformate (Sigma Aldrich, #C77007) and 3 equivalents of DIPEA in dichloromethane. The reaction was agitated with argon gas for 12 h, then washed with dichloromethane. Cleavage of the cholesteryl-PEG4-COOH was carried out in 100 ml 5% trifluoroacetic acid (TFA) in dichloromethane with agitation for 2 hours. The resulting solution was dried by rotary evaporation, then purified by flash chromatography (Biotage ZIP Sphere column) using a gradient of ethanol in dichloromethane.

Cholesteryl-PEG4-COOH was then dissolved in acetonitrile to a concentration of 800 mM before adding 1.1 equivalents of N,N'-disuccinimidyl carbonate (Sigma Aldrich, #225827) followed by 0.8 equivalents of triethylamine. The solution was heated to 45° C. and stirred for 60 min before purification by flash chromatography (Biotage ZIP sphere column) using a gradient of ethanol in dichloromethane. The resulting product was dried extensively by rotary evaporation to yield a viscous yellow oil.

Synthesis of CPT31

PIE12-2 monomer (Ac-HPCDYPEWQWLCELG-PEG4-K—NH$_2$) was synthesized by Ambiopharm, Inc. (North Augusta, S.C.) using all D-amino acids. PIE12-2 was suspended in dimethylacetamide buffered with triethylamine (150 mM) to a concentration of 20 mM. To this, FMOC-PEG28-triNHS was added to a concentration of 6.06 mM. The reaction proceeded for 2 h at room temperature before piperdine was added to 30% and the reaction was mixed for 40 min to remove the Fmoc group. NH$_2$-PEG28-PIE12-2 trimer was then purified by RP-HPLC (Waters X-Bridge C18 column). This product (10 mM) was reacted with cholesteryl-PEG4-NHS (12 mM) in dimethylacetamide buffered by triethylamine (150 mM) for 90 min and purified by RP-HPLC (Waters X-Bridge C18 column) to generate CPT31 (cholesterol-PIE12-2-trimer with PEG32 fourth-arm spacer).

Pseudovirion Entry Assay

Pseudovirion assays were performed as previously described (Welch et al., 2010, J. Virol. 84:11235-44; Welch et al., 2007, Proc. Natl. Acad. Sci. 104:16827-16833, each of which is incorporated herein by reference in its entirety). Briefly, a six-point dilution series of each inhibitor was generated in quadruplicate on HOS-CD4-CXCR4 (for HXB2) or HOS-CD4-CCR5 (for JRFL) monolayers in 96 well plates, after which HXB2 (X4) or JRFL (R5) luciferase reporter pseudovirions were added. After 2 days, cells were lysed using GloLysis buffer (Promega) and BrightGlo luciferase substrate (Promega) was added. Luminescence was read on a PolarStar Optima (BMG) plate reader and normalized to uninhibited controls. Inhibition curves were plotted and fit to a standard IC$_{50}$ equation for normalized data [(1−c/(IC$_{50}$+c)], weighting each point by its standard error using KaleidaGraph (Synergy Software). Reported IC$_{50}$ values are the average of at least two independent quadruplicate assays.

Breadth Assay

Breadth assays were performed against the International Reference Panel of HIV-1 Isolates (NIH AIDS reagent program). CPT31 was tested at 1 and 10 nM in TZM-Bl cell monolayers in 96 well plates in the presence of 8 µg/ml DEAE dextran against each of the 59 viruses examined. Virus was incubated with cells and inhibitor for 30 h, then cells were lysed using 50 µl GloLysis buffer (Promega) and 50 µl BrightGlo (Promega) was added. Luminescence was read on a PolarStar Optima (BMG) plate reader and normalized to uninhibited controls. Reported values are percent inhibition compared to uninhibited values and are the average of at least two independent assays of 4 replicates each.

Rodent Pharmacokinetics

For PIE12 monomer conjugates, in-life studies were performed by Invitek (Hayward, Calif.). Trimeric conjugate in-life studies were performed at Navigen (Salt Lake City, Utah). For each study, three Sprague Dawley rats (0.22-0.44 kg) were dosed as described in table 3. At each timepoint, plasma was obtained using lithium heparin. For CPT24, CPT24-5 kD and CPT31, in life studies were conducted at Calvert Laboratories Inc. (Scott Township, Pa.). Three male rats per route were dosed with either CPT24 or CPT24-5 kD formulated at 2 mg/mL in 50 mM HEPES (pH 7.4). For both subcutaneous (SC) and intravenous (IV) administration, a dose of 1 mg/kg was delivered and plasma (K$_2$EDTA)

samples were collected at time points from 5 minutes to 24 hours for the IV group and 15 minutes to 48 hours for the SC group. Two male rats per route were dosed with CPT31 formulated at 2 mg/mL in 50 mM HEPES (pH 7.4). For both subcutaneous and intravenous administration, a dose of 1 mg/kg was delivered and plasma ($K_2$EDTA) samples were collected at time points from 5 minutes to 16 hours for the IV group and 15 minutes to 24 hours for the SC group. Plasma samples were stored at −80° C. and shipped prior to bioanalysis.

Non-Human Primate Pharmacokinetics

In-life was performed by Calvert Laboratories (Scott Township, Pa.). One group of three male cynomolgus monkeys (3.4-3.9 kg at first dosing) were administered CPT31 (2 mg/ml in 50 mM HEPES, pH 7.4) as a single bolus injection into a saphenous vein at a dose of 1 mg/kg (0.5 ml/kg). Upon IV dosing, 1 ml blood samples were collected at 0.083, 0.167, 0.25, 0.5, 1, 2, 4, 8, 16 and 24 h post-dose into chilled tubes containing $K_2$EDTA, mixed by inversion, and centrifuged (3000 rpm, 4° C., 15 min) to isolate plasma. Plasma was stored at −80° C. until bioanalysis.

Following a 13-day washout period, study animals were administered a single subcutaneous dose of CPT31 (10 mg/ml in 50 mM HEPES, pH 7.4) into the loose skin of the back between the shoulder blades at a dose of 3 mg/kg. Plasma samples were collected at pre-dose, 0.25, 0.5, 1, 2, 4, 8, 16, 24 and 48 hours post-dose. Collected blood samples were treated as described above. The pre-dose sample confirmed drug levels were below the lower limit of quantification (5.00 nM).

Quantitative Bioanalysis

PIE12-Trimer Conjugates

Samples were spiked with an internal standard then precipitated with two volumes of 98% acetonitrile/2% Formic acid. Supernatants were analyzed by LC/MS/MS using an Agilent HPLC system (Waters X-Bridge BEH C18 column) paired to an AB Sciex API 3000 triple-quad mass spectrometer using MRM methods. Lipid conjugates required lower source temperatures (300° C. vs 500° C.) for improved reproducibility. For all studies the column was regenerated after each group of three rats by running an isocratic gradient of 25% water/25% methanol/25% isopropanol/25% acetonitrile for 30 min to remove retained phospholipids.

Mass transitions were as follows for each analyte: PIE12-trimer (1431.7/180.1), palmitate-PEG24-PIE12-trimer (1466.5/554.4), C16-PEG24-PIE12-timer (1450.1/453.4), C18-PEG24-PIE12-trimer (1454.5/481.3) and cholesterol-PEG24-PIE12-trimer (1474.2/1694.9).

CPT24 in Rat Plasma-Calvert Study

Fifty microliter aliquots of plasma for each time point was precipitated with 3 volumes of ice-cold acetonitrile containing 2% formic acid (v/v) and 1.56 μM CPT12 as internal standard. Following centrifugation, 8 μL of supernatant was injected onto a Poroshell 300 SB-C8 column (2.1×75 mm, 5 μm) (Agilent Technologies). Analyte (CPT24) and internal standard (CPT12) were separated on an Agilent 1290 UHPLC system using a gradient consisting of 0.2% formic acid in 5 mM aqueous ammonium acetate buffer and 0.2% formic acid in acetonitrile/isopropanol (1:1) at a flow rate of 0.65 mL/min. The column temperature was maintained at 70° C. Ions were formed by a dual electrospray source operated in positive-ion mode and detected on an Agilent quadrupole time-of-flight (Q-TOF) mass spectrometer (6540A). Extracted-ion chromatograms were processed with MassHunter Quantitative Analysis software (Agilent V. B.06). A m/z of 1476.7156 with a m/z window of 40 ppm was used to extract the peak area for CPT24. This ion corresponds to the second most abundant C13 isotope peak in the 6+ charge state cluster and represents the M+7 isotope of the $(M+5H+NH4)^{6+}$ ion cluster. A m/z of 1662.5882 with a m/z window of 200 ppm was used to extract the peak area for CPT12. This ion corresponds to the most abundant C13 isotope peak in the 5+ charge state cluster and represents the M+6 isotope of the $(M+5H)^{5+}$ ion cluster. Plasma concentrations were determined from peak area ratio of analyte/IS compared against a 8-point calibration curve spanning a concentration range of 15.6 nM to 2,000 nM.

CPT24-5 kD in Rat Plasma-Calvert Study

Fifty microliter aliquots of plasma for each time point was precipitated with 2.5 volumes of ice-cold acetonitrile containing 2% trifluoroacetic acid (v/v) and 370 nM CPT12 as internal standard. Following centrifugation, 10 μL of supernatant was injected onto a Poroshell 300 SB-C8 column (2.1×75 mm, 5 μm) (Agilent Technologies). Analyte (CPT24) and internal standard (CPT12) were separated on an Agilent 1290 UHPLC system using a gradient consisting of 0.2% formic acid in 10 mM aqueous ammonium acetate buffer and 0.2% formic acid in acetonitrile/isopropanol (1:1) at a flow rate of 0.70 mL/min. The column temperature was maintained at 70° C. Ions were formed by a dual electrospray source operated in positive-ion mode and detected on an Agilent quadrupole time-of-flight (Q-TOF) mass spectrometer (6540A). Extracted-ion chromatograms were processed with MassHunter Quantitative Analysis software (Agilent V. B.06). Due to the polydispersity of the 5 kD PEG, three separate m/z ions of 1074.2127, 1157.9981 and 1159.3843 each with a m/z window of 200 ppm were used to extract the peak area for CPT24-5 kD. These ions correspond to the 14+ and 13+ charge states. A m/z of 1662.5882 with a m/z window of 100 ppm was used to extract the peak area for CPT12. This ion corresponds to the most abundant C13 isotope peak in the 5+ charge state cluster and represents the M+6 isotope of the $(M+5H)^{5+}$ ion cluster. Plasma concentrations were determined from peak area ratio of analyte/IS compared against a 8-point calibration curve spanning a concentration range of 15.6 nM to 2,000 nM.

CPT31 in Rat Plasma-Calvert Study

Fifty microliter aliquots of plasma for each time point was precipitated with 5 volumes of ice-cold acetonitrile containing 1% formic acid (v/v). No internal standard was used. Following centrifugation, 1 μL of supernatant was injected onto a Poroshell 120 EC-C8 column (2.1×5 mm, 2.7 μm) (Agilent Technologies). Analyte (CPT31) was separated on an Agilent 1290 UHPLC system using a gradient consisting of 20 mM aqueous ammonium bicarbonate buffer and acetonitrile at a flow rate of 0.45 mL/min. The column temperature was maintained at 40° C. Ions were formed by a dual jet spray electrospray source operated in positive-ion mode and detected on an Agilent quadrupole time-of-flight (Q-TOF) mass spectrometer (6540A). Extracted-ion chromatograms were processed with MassHunter Quantitative Analysis software (Agilent V. B.06). A m/z of 1508.7473 with a m/z window of 40 ppm was used to extract the peak area for CPT31. This ion corresponds to the second most abundant C13 isotope peak in the 6+ charge state cluster and represents the M+7 isotope of the $(M+5H+NH4)^{6+}$ ion cluster. Plasma concentrations were determined from the peak area of analyte compared against a 8-point calibration curve spanning a concentration range of 5.00 nM to 4,000 nM.

CPT31 in Monkey Plasma-Calvert Study

The internal standard, CPT31-IS was synthesized with an additional glycine on each PIE12-2 monomer (three in total), increasing the molecular mass by 171.1 Da. Plasma samples (200 µl) were spiked with CPT31-IS to a concentration of either 60 or 150 nM, then precipitated in 2% NH₄OH in acetonitrile (500 µl). Following centrifugation, the supernatant was applied to a strong anion exchange solid-phase extraction 96-well plate (SOLAµ SAX, 2 mg/ml 96-well plate). The anion exchange plate was first conditioned with 400 µl of 2% NH₄OH in methanol, followed by 400 µl of 2% NH₄OH in water. The precipitated supernatant (500 µl) was then loaded into each well, followed by washing with 500 µl of 2% NH₄OH in water, then 500 µl of methanol. Sample was eluted using two 50 µl aliquots of 2% formic acid in methanol.

LC-MS analysis was conducted using an Agilent Infinity 1290 HPLC system paired to an Agilent 6450A Q-TOF mass spectrometer equipped with a Dual Jet Spray ESI source. Sample (1 µl) was injected at a flow rate of 0.45 ml/min on a Thermo Scientific Accupore 150 C4 column (2.1×50 mm, 2.6 µm), using a gradient of 20 mM ammonium bicarbonate (pH 7.9) in water and acetonitrile. Samples were analyzed against a standard curve of CPT31 from 5.00-2,000 nM.

Pharmacokinetic Data Fitting

All bioanalytical data was fit using noncompartmental analysis with Phoenix edition v.6.4 WinNonlin (Pharsight, Cary, N.C.).

Results

Figure 2:
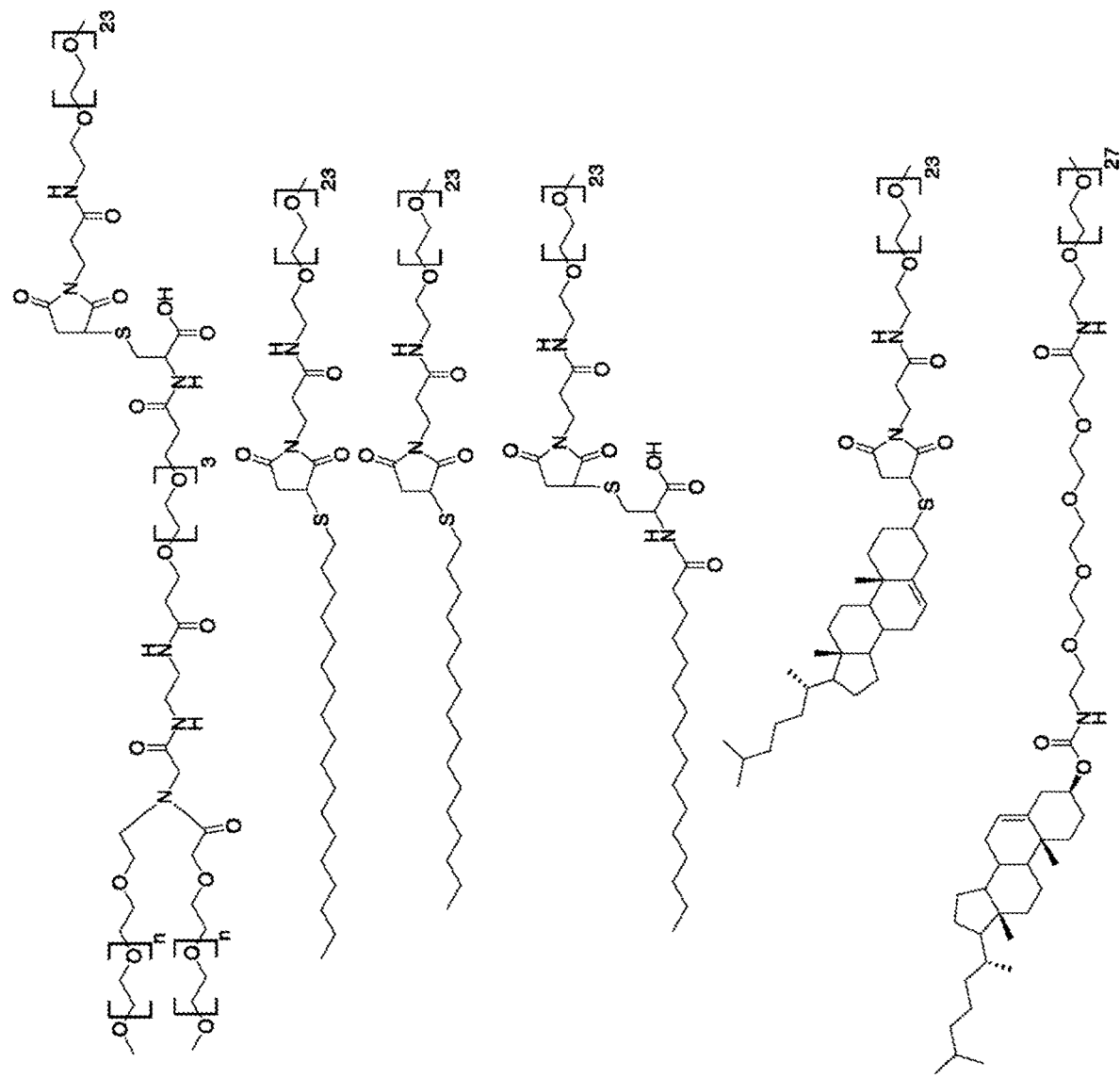
FIG. 2 depicts schematics of selected pharmacokinetic (PK) enhancing moieties on a fourth arm reading from top to bottom: a Y-branched PEG (PEG40) linked to a PEG24 spacer; C18 alkane chain linked to a PEG24 spacer; C16 alkane chain linked to a PEG24 spacer; palmitate linked to a PEG24 spacer; thiocholesterol linked to a PEG24 spacer; and cholesteryl linked to PEG4 chain and PEG28 chain in series.

PIE12-trimer comprises three PIE12 monomers each containing a unique primary amine (epsilon amino of a C-terminal Lys), coupled to a scaffold using a homobifunctional PEG4-NHS ester crosslinker. The 4$^{th}$ arm of our previously reported 4-arm scaffold is composed of a PEG24 spacer that terminates in a maleimide (thiol-reactive) group (FIG. 2). The orthogonal maleimide reactivity provides a convenient way to couple various conjugates to PIE12-trimer to explore their effect of potency and PK properties of the molecule. Conjugates were selected from clinically successful and promising preclinical PK-enhancing moieties (discussed below).

TABLE 1

PIE12 D-peptides

| Peptide | Sequence (all D-amino acids) | SEQ ID NO: # |
|---|---|---|
| PIE12 | Ac-HPCDYPEWQWLCELGK-NH₂ | 1 |
| PIE12-PEG₄ | Ac-HPCDYPEWQWLCELGK(PEG₄)-NH₂ | 2 |
| PIE12-2 | Ac-HPCDYPEWQWLCELG-PEG₄-K-NH₂ | 3 |

PEGylation

PEGylation is a validated strategy for enhancing PK properties, based upon the results of eleven FDA-approved products. PEG conjugation improves half-life primarily through increasing drug size to reduce renal filtration, but can also decrease proteolysis and immunogenicity for susceptible proteins. The primary challenge of PEGylation is adding sufficient PEG to increase half-life without impairing the activity of the conjugate (e.g., steric occlusion of a binding site). Most approved PEGylated compounds feature 20-40 kDa of conjugated PEG, through single or multiple attachments. PEG conjugation is particularly effective, as PEG has a large hydrodynamic radius relative to its mass.

PEGASYS, a PEG-conjugated interferon used in the treatment of hepatitis C virus (HCV), is a particularly well-studied PEGylated protein. It features a single branched 40 kDa PEG, advantageous because branched PEG chains have been shown to better increase half-life and preserve activity by protecting against proteolysis when compared to mass-equivalent straight chain PEGs (Fee, Biotech and bioengineering)(Reddy, Adv drug deliv. Reviews). The IV half-life of PEGASYS is extended ~20-fold compared to unconjugated interferon (65 vs 3.8 h in humans), and its volume of distribution is 5-fold lower. Therefore clearance is slowed 100-fold (Fishburn, J. of Pharm sci), enabling once-weekly subcutaneous administration.

A similar 40 kDa Y-branched PEG was coupled to the PIE12-trimer (PEG40-PIE12-trimer) in an attempt to enhance its PK properties. Conjugation of PEG40 to PIE12-trimer reduced potency 13- and 34-fold (HXB2 and JRFL, respectively, Table 2), likely due to steric interference surrounding the gp41 pocket (Hamburger, JBC, Eckert, Protein Sci). In PEGASYS, the same PEG reduces activity 14-fold while increasing circulating half-life 25-fold (Fishburn, J. of Pharm Sciences). A similar ~15-fold increase in circulating half-life was observed (data not shown) when PEG40 was attached to PIE12-monomer and would expect a similar circulating half-life in the context of PIE12-trimer. While this significant increase in half life is favorable despite the loss of potency and ~5-fold increase in mass of the molecule, PEG40-PIE12-trimer was not the most favorable compound tested for either weekly dosing or monthly dosing (via depot formulation), and it was not pursued further.

TABLE 2

Antiviral Potency of Various PIE12 Conjugates

| Compound | HXB2 (nM) | JRFL (nM) |
|---|---|---|
| PIE12-trimer | 0.72 ± 0.04* | 2.1 ± 0.28* |
| PEG40-PIE12-trimer | 9.5 ± 1.4 | 71 ± 12 |
| Palm-PIE12-trimer | 0.225 ± 0.008 | 0.540 ± 0.041 |
| C16-PIE12-Trimer | 0.09 ± 0.014* | 0.11 ± 0.012* |
| C18-PIE12-trimer | 0.054 ± 0.018* | 0.087 ± 0.012* |
| CPT24 | 0.013 ± 0.0013* | 0.019 ± 0.003* |
| CPT24-5kD | ND | 0.026 ± 0.007 |
| CPT31 | ND | 0.015 ± 0.007 |

(*from Francis, et al. Bioconjugates)

Acylation

PK-enhancement by acylation is thought to be primarily based on the strong interaction (mid-to-low nM) (Spector, J. of Lipid research/Richieri, Biochemistry/Richieri, J. of Lipid research) of fatty acids with human serum albumin (HSA), which circulates for 19 days. Other PK benefits of acylation include self-association that prolongs absorption from the subcutaneous space (Nordisk: Havelund, Pharm research) and interaction with cell membranes. One example of acylation prolonging half-life is Victoza (Liraglutide), a GLP-1 analogue conjugated to palmitate, which enables once-daily subcutaneous dosing for treatment of type 2 diabetes.

Physiologically, free (not esterified to glycerol) fatty acids (FFA) circulate bound to HSA, and palmitate and stearate (fatty acids with 16 or 18 carbon atoms, respectively) are the predominate forms of circulating FFAs (Tuei, life sciences). Notably, FFAs do not bind significantly to any other circulating particles, including low-density lipoproteins (LDL) (Spector, J. of lipid research), and FFAs bind distinct HSA sites from most small molecules.

Conjugation of palmitate to PIE12-trimer (palm-PIE12-trimer) was accomplished using Cys as a bridge to generate necessary reactivity with our 4-arm 3-{2-Amino-3-(2-carboxyethoxy)-2-[(2-carboxyethoxy)methyl]propoxy}propionic acid scaffold. Palmitoylation resulted in a modest 3-4-fold increase in potency (HXB2 and JRFL strains) compared to unconjugated PIE12-trimer (Table 2). Palm-PIE12-trimer also improved PK properties by increasing IV half-life>3-fold and reducing clearance ~14-fold. Furthermore, Palm-PIE12-trimer was fully bioavailable upon SC dosing with an ~3-fold extension of apparent half-life (based on terminal phase elimination) by this dosing route.

these interactions are weak (Charbonneau, J. of phys chem) (Peng, Protein and peptide letters) and transient (Francis, Bioconjugates).

Commercially available thiocholesterol was coupled directly to the $4^{th}$ arm maleimide of 3-{2-Amino-3-(2-carboxyethoxy)-2-[(2-carboxyethoxy)methyl]propoxy}propionic acid based scaffold (cholesterol-PIE12-trimer with PEG24 fourth-arm spacer, CPT24), and this conjugate exhibited the greatest improvement in potency, showing a remarkable 110-fold improvement in potency

TABLE 3

Median IV and SC plasma PK parameters of PIE12-trimer and conjugates in rats

| Compound | Route of Admin | Dose (mg/kg) | $T_{1/2}$ (hr) | $T_{max}$ (hr) | $C_0$ or $C_{max}$ (nM) | AUC (0-inf) (hr * nM) | Vz (obs) (mL/kg) | Cl (obs) (mL/hr/kg) | F (%) |
|---|---|---|---|---|---|---|---|---|---|
| PIE12-trimer | IV | 1.0 | 0.55 | NA | 275 | 168 | 700 | 835 | NA |
| | SC | 1.0 | 0.81 | 0.5 | 80 | 208 | NA | NA | 96 |
| palm-PIE12-trimer | IV | 1.2 | 1.83 | NA | 2242 | 2241 | 140 | 61 | NA |
| | SC | 1.2 | 2.23 | 1.0 | 585 | 2313 | NA | NA | 103 |
| C16-PIE12-trimer | IV | 1.0 | 0.93 | NA | 1875 | 1155 | 140 | 100 | NA |
| | SC | 1.0 | 1.18 | 1.0 | 192 | 442 | NA | NA | 38 |
| C18-PIE12-trimer | IV | 1.0 | 1.05 | NA | 900 | 766 | 230 | 150 | NA |
| | SC | 1.0 | 1.39 | 2.0 | 196 | 713 | NA | NA | 93 |
| CPT24 | IV | 1.0 | 1.77 | NA | 1112 | 2394 | 130 | 47 | NA |
| | SC | 1.0 | 2.71 | 4.0 | 304 | 1748 | NA | NA | 73 | n = 3,
NA = not applicable

Alkylation

Based on previous work that identified a fatty acid's aliphatic chain as the critical moiety for albumin interaction (Spector, J. of lipid research), alkane conjugation was also explored. Alkanes only differ from fatty acyl groups by the absence of a single terminal carbonyl group, and commercially available thiol-alkanes made synthesis straightforward using the maleimide chemistry of the fourth arm on the scaffold.

Conjugation of thio-alkanes with fatty chain lengths of either 16 or 18 carbons (C16-PIE12-trimer or C18-PIE12-trimer, respectively) gave similar results in terms of both a substantial potency boost (8- to 24-fold) as well a modest increase in half-life upon IV or SC dosing, but clearance rates decreased more significantly, possibly due to increased plasma protein binding.

The difference in half-life between the palmitoylated and thio-alkylated conjugates is surprising. The additional hydrophobicity of C16-PIE12-trimer presumably increases membrane affinity, which could be the mechanism for improved antiviral potency compared to palm-PIE12-trimer. Interestingly, the inhibitor containing the more hydrophobic alkane, C18-PIE12-trimer also showed prolonged absorption from the subcutaneous space, but this effect did not increase the apparent half-life upon SC dosing compared to palm-PIE12-trimer, since the latter had a lower clearance rate.

Cholesterol Conjugation

Cholesterol conjugation of an HIV C-peptide inhibitor increases half-life in mice (Ingallinella, PNAS). As a newer strategy for which there are no FDA-approved examples, the mechanism of this effect is unclear. A combination of cell membrane and HSA association may be involved, however against the JRFL strain. CPT24 also showed the greatest improvement in PK, increasing IV and SC half-life>3-fold (to 1.8 h and 2.7 h, respectively) and reducing the clearance rate ~18-fold.

Though cholesterol is known to interact with HSA, its affinity is lower than that of palmitate. Therefore, CPT24's enhanced PK profile is likely due to membrane interaction (Ingallinella et al, PNAS). This explanation is consistent with the prolonged absorption rate of CPT24 from the subcutaneous space (4 h $T_{max}$ in rat), as well as the potency boost associated with cholesterol, which is known to concentrate in lipid rafts, the sites of viral entry.

In an effort to determine if increasing the size of the PEG group would further reduce clearance, synthesized CPT24-5 kD was synthesized, which includes 5 kDa of linear polydisperse PEG between PIE12-trimer and thiocholesterol. It has been previously shown that increasing the length of the PEG spacer between thiocholesterol and PIE12-trimer has little effect on potency, and, as expected, the potency of CPT24-5 kD is comparable to CPT24 (Table 2).

All of the PK data presented in Table 3 was generated using the same animal protocols and similar bioanalytical methods. Different animal protocols and improved bioanalytical methods were used to generate the data in Table 4 (all PK fitiing was performed using WinNonlin software). The PK study for CPT24 was repeated using the updated protocols/methods. The repeat CPT24 data is similar to the original except for $C_0$ and its derived parameters, likely explained by earlier sampling times for data collected in Table 4.

For both IV and SC administration, the added 5 kDa PEG resulted in a prolonged half-life (3.5-fold and 1.8-fold, respectively) when compared to CPT24 (Table 4). However, bioavailability for CPT24 was greater than CPT24-5 kD (51% vs 34%, respectively), suggesting that the added PEG mass is responsible for additional metabolism in the subcutaneous space or lymphatic system. Taken together, the beneficial PK effects of the added PEG were insufficient to warrant the added complexity associated with the 5 kDa PEG, which, unlike the original PEG24 $4^{th}$ arm, is polydisperse.

dimer and the correct trimer final product. Additionally, the location of the PEG linker on each of the three peptide arms was moved from the Lys sidechain (PIE12GK-PEG4) that required orthogonal protection during solid phase peptide synthesis (SPPS), to the peptide backbone (PIE12G-PEG4-K) where no additional reagents or synthetic steps were required. The redesigned molecule, CPT31, has a $4^{th}$ arm that separates cholesterol from the trimer by 32 PEG units

TABLE 4

Median IV and SC plasma PK parameters of cholesterol conjugates of PIE12-trimer in rats

| Compound | Route of Admin | Dose (mg/kg) | $T_{1/2}$ (hr) | $T_{max}$ (hr) | $C_0$ or $C_{max}$ (nM) | AUC (0-inf) (hr * nM) | Vz (obs) (mL/kg) | Cl (obs) (mL/hr/kg) | F (%) |
|---|---|---|---|---|---|---|---|---|---|
| CPT24* | IV | 1.0 | 1.62 | NA | 4526 | 4660 | 57 | 24 | NA |
|  | SC | 1.0 | 3.88 | 2 | 395 | 2394 | NA | NA | 51.4 |
| CPT24-5 kD* | IV | 1.0 | 5.62 | NA | 1098 | 4578 | 118 | 14.6 | NA |
|  | SC | 1.0 | 7.21 | 4 | 89 | 1557 | NA | NA | 34.0 |
| CPT31† | IV | 1.0 | 3.25 | NA | 2953 | 3844 | 134 | 29 | NA |
|  | SC | 1.0 | 5.4 | 2 | 261 | 2110 | NA | NA | 55 |

*n = 3,
†n = 2,
NA = not applicable

Redesign of Chol-PIE12-Trimer

As described above, the first iteration of the PEG scaffold contained three arms functionalized with NHS ester for reaction with a unique primary amine on PIE12, while the fourth arm was functionalized with a maleimide group for reaction with thiols. While functional and efficient for rapidly testing a variety of conjugates, this scaffold is not ideal as a drug substance since the maleimide-thiol reaction introduces a heterogeneous stereocenter.

Therefore, the scaffold was redesigned to avoid introduction of a stereocenter while simultaneously simplifying synthesis, improving yield and scalability, and reducing cost (of both the scaffold and final product). This revised scaffold comprises three short arms functionalized with NHS esters and a fourth arm (a high-quality monodisperse PEG28) terminating with an F-moc-protected unique primary amine. After reaction of PIE12-2 monomer with the three NHS esters and removal of the F-moc on the $4^{th}$ arm, this trimer intermediate is purified by HPLC. Next, cholesterol-PEG$_4$-NHS ester is conjugated to the primary amine on the fourth arm. Purification of the trimer intermediate simplifies synthesis since the main contaminant, PIE12-2 dimer (caused by competing hydrolysis of the NHS esters on the scaffold during trimerization), can be readily separated by HPLC purification prior to conjugation with cholesterol. After cholesterol conjugation, there is a dramatic shift to a later HPLC retention time, but much less separation between (vs. 24 in CPT24), lacks any heterogenous stereocenters, and is easier and more efficient to produce. Like CPT24, CPT31 is soluble in standard aqueous buffers (e.g., PBS, HEPES) at physiological pH to ~40 mg/mL.

Comparison of CPT31 to CPT24 unexpected showed that the modifications result in improved PK properties. CPT31's IV half-life increases to an average of 3.25 h from 1.62 h in rats for CPT24, and to 5.4 h for SC dosing from 3.8 h for CPT24 (Table 4). A possible explanation for this observation is that the bulky maleimide group adjacent to thiocholesterol in CPT24 hinders cholesterol insertion into the membrane. The potency of CPT31 against the JRFL strain also modestly improved from 19 pM to 15 pM, providing further evidence that the modified cholesterol linkage improves membrane association.

The PK profile of CPT31 in non-human primates (NHPs) was determined to support future efficacy studies in this definitive animal model. Three male cynomolgus monkeys were dosed IV at 1 mg/kg. After a 2 week wash out period, these animals were dosed SC at 3 mg/kg (a potential high dose to evaluate therapeutic efficacy in NHPs). Importantly, no adverse events were observed. These data are summarized in Table 5. CPT31 has more favorable PK properties in NHPs than predicted from simple allometric scaling of the rat data, with longer IV and SC half-life, increased bioavailability, and reduced clearance.

TABLE 5

Median IV and SC plasma PK parameters of CPT31 in Male Cynomolgus Monkeys

| Compound | Route | Dose (mg/kg) | $T_{1/2}$ (hr) | $T_{max}$ (hr) | $C_0$ or $C_{max}$ (nM) | AUC (0-inf) (hr * nM) | Vz (obs) (mL/kg) | Cl (obs) (mL/hr/kg) | F (%) |
|---|---|---|---|---|---|---|---|---|---|
| CPT31 | IV | 1.0 | 7.4 | NA | 3110 | 11619 | 97 | 9.5 | NA |
|  | SC | 3.0 | 18.8 | 8 | 922 | 29434 | NA | NA | 80.4 | n = 3,
NA = not applicable

To examine the efficacy of CPT31 against representative replication competent HIV strains, inhibition of infection at 1 nM and 10 nM against 59 international primary isolates consisting of 10 viruses each from clades A, B, and D, as well as circulating recombinant forms AE and AG, and 9 from clade C (International Panel of HIV-1 isolates, NIH AIDS Reagent Program) was tested, with data shown in Table 6. At 1 nM, CPT31 provided excellent inhibition (>90%) of 49 of the 59 tested strains. Of those not inhibited >90% at 1 nM, 4 were inhibited greater than 90% at 10 nM. Of those strains not inhibited, two have a well characterized pocket mutation (Q577R) that ablates pocket binding. All poorly inhibited strains were either clade C or D. Many of the poorly inhibited strains had very low titer, and the inhibitory activity of CPT31 may be underestimated for those strains. This illustrates the excellent breadth of CPT31 against a broad panel of representative strains.

TABLE 6

Inhibitory activity of CPT 31 against 60 International HIV-1 Primary isolates.

| Virus | CLADE | 1 nM inhibition | 10 nM inhibition |
|---|---|---|---|
| 92UG029 | A | 95.2 | 98.2 |
| KER2008 | A | 84.1 | 85.3 |
| KER2018 | A | 94.8 | 97.5 |
| KNH1088 | A | 98.5 | 99.6 |
| KNH1135 | A | 80.6 | 83.4 |
| KNH1144 | A | 78.2 | 80.6 |
| KNH1207 | A | 92.1 | 98.2 |
| KNH1209 | A | 94.3 | 95.2 |
| KSM4030 | A | 93.6 | 95.6 |
| 93RW024 | A | 97.0 | 99.3 |
| 0503M02138 | AE | 95.2 | 98.0 |
| CM235/GS020 | AE | 81.8 | 98.7 |
| CM244 | AE | 95.4 | 99.5 |
| CM240/GS022 | AE | 83.8 | 95.0 |
| NI1046 | AE | 99.1 | 99.7 |
| NI1052 | AE | 98.0 | 99.7 |
| NI1149 | AE | 92.9 | 97.4 |
| NP1251 | AE | 97.0 | 98.4 |
| NP1525 | AE | 98.8 | 99.3 |
| NP1695 | AE | 95.7 | 97.0 |
| 55815 | AG | 98.8 | 99.5 |
| CAM0002 | AG | 95.6 | 99.7 |
| CAM0013 | AG | 98.4 | 99.7 |
| CAM0014 | AG | 98.8 | 99.5 |
| CAM0015 | AG | 96.0 | 97.0 |
| CAM0005 | AG | 98.4 | 99.8 |
| CAM0008 | AG | 96.8 | 99.7 |
| CAM1475MV | AG | 98.3 | 98.8 |
| CAM1970LE | AG | 97.3 | 98.5 |
| DJ263/GS003 | AG | 96.7 | 99.2 |
| 873 | B | 93.6 | 98.7 |
| 3343IN | B | 97.6 | 99.1 |
| Ba-L | B | 96.9 | 99.8 |
| BK132/GS009 | B | 99.7 | 99.8 |
| BX08 | B | 94.2 | 99.5 |
| BZ167 | B | 99.4 | 99.8 |
| MN/H9 | B | 99.3 | 100.0 |
| NP1538 | B | 95.0 | 99.4 |
| US1/GS0004 | B | 95.3 | 97.7 |
| US4/GS007 | B | 91.1 | 98.7 |
| 56313 | C | 97.9 | 99.3 |
| 20635-4 | C | 99.0 | 99.6 |
| PBL286 | C | 95.8 | 99.0 |
| PBL288 | C | 3.0 | 12.0 |
| SE364/GS015 | C | 91.6 | 97.7 |
| SM145/GS016 | C | 30.6 | 75.7 |
| TZA246 | C | 98.3 | 98.4 |
| TZA68 | C | 97.7 | 99.7 |
| TZBD9/11 | C | 84.7 | 85.4 |
| 57128 | D | 35.2 | 37.3 |
| 301965 | D | 96.1 | 97.7 |
| 93UG065 | D | 93.7 | 94.4 |
| A03349M1 | D | 93.6 | 99.5 |
| A07412M1 | D | 92.0 | 96.7 |
| A08483M1 | D | 69.2 | 72.3 |
| D26830M4 | D | 95.3 | 98.5 |
| E08364M4 | D | 50.7 | 58.6 |
| J32228M4 | D | 96.1 | 98.0 |
| NKU3006 | D | 97.2 | 99.8 |

Summary

PEGylation yields the greatest PK enhancement in terms of increasing half-life, but at the cost of potency. Palmitate conjugation improves half-life and potency modestly, but to a lesser degree than cholesterol. Alkane conjugation improves potency, but does little to improve half-life. Of the conjugates tested, cholesterol most significantly improved potency and PK properties of PIE12-trimer, while also maintaining good solubility.

Of unknown significance is the decreased volume of distribution created by each conjugation because it is not clear which tissue compartments must be accessed for successful inhibition and to block transmission of HIV. However, it is clear that Fuzeon is highly HSA bound (Trimeris, 1-18), has a reduced volume of distribution in humans, and successfully inhibits HIV.

The redesigned drug candidate, CPT31, incorporates design elements that simplify its synthesis, improve scalability, and eliminate heterogeneity compared to the previous compound, CPT24. Furthermore, CPT31 has unexpectedly improved PK as well as increased antiviral potency.

First, the PIE12 peptide sequence was altered. Starting from the D-peptide monomer sequence for PIE12 (Ac-HPCDYPEWQWLCELGK-NH2, all D-amino acids (SEQ ID NO:1)), CPT24 utilized a polyethylene glycol (PEG) spacer (PEG4) attached to each D-peptide via an amide bond at the epsilon amino group of the C-terminal D-lysine side chain. This is noted as "PIE12-PEG4" in FIG. 3A. The attachment of PIE12-PEG4 to the multimer scaffold is achieved by condensation between the terminal amino group of the PEG4 and the carboxyl group of the scaffold, producing an amide bond (FIG. 4A). Though functional, the synthesis of PIE12-PEG4 is more complex synthetically. As a result, yield of the peptide is lower, and synthesis requires non-standard amino acid side chain protection at the C-terminal D-lysine.

For the synthesis of CPT31, the PIE12 sequence was altered to improve synthetic yields and reduce complexity. To achieve this, the PEG4 linker was moved to the peptide backbone, becoming a residue in the PIE12 peptide sequence. The CPT31 PIE12 variant, denoted "PIE12-2" in FIG. 3B, utilizes a PEG4 spacer between the C-terminal D-lysine and the adjacent glycine. The attachment of PIE12-2 to the scaffold is thus achieved by an amide bond between the epsilon amino group of the C-terminal D-lysine and the carboxyl group of the scaffold by condensation (FIG. 4B), avoiding the need for an orthogonal Lys protecting group.

The second change is in the trimer scaffold of CPT24 vs. CPT31. Both share a tetrahedral carbon core, but differ in the composition of the three short arms that attach the peptides. This difference is highlighted in FIG. 5. CPT24 uses a 3-{2-Amino-3-(2-carboxyethoxy)-2-[(2-carboxyethoxy) methyl]propoxy}propionic acid scaffold (FIG. 5A.), whereas CPT31 uses a 4-Amino-4-(2-carboxyethyl)heptanedioic acid scaffold (FIG. 5B). This change results in large-scale synthesis at a lower cost.

The third change is a difference in the composition of the fourth PEG arm that joins the peptide trimer to the cholesterol scaffold. CPT24 uses a continuous PEG24 chain to join the thiocholesterol to the peptide trimer, whereas CPT31 uses two PEG chains in series. The first PEG chain, PEG28, is connected to the peptide scaffold by an amide bond. The second PEG chain, PEG4, is joined to the PEG28 by an amide bond as well as to the cholesterol by a carbamate. This difference can be seen in FIG. 3B. This change results in significant improvement in the ability to purify the peptide trimer prior to addition of cholesteryl-PEG4-NHS. In the synthesis of CPT24, thiocholesterol is conjugated subsequent to peptide addition, but in the same reaction. This makes purification of the cholesterolated trimer difficult, as the cholesterol addition makes discrimination between the cholesterolated dimer (a major contaminant) and trimer (the desired product) difficult, reducing yield. In the synthesis of CPT31, PIE12-2 D-peptides are conjugated to the scaffold, and the peptide trimer is purified prior to the addition of cholesterol, allowing for significant gains in yield and purity. Furthermore, the slight elongation of the fourth PEG arm yields a ~20% improvement in antiviral potency (from 19 pM to 15 pM) as a result of more adequately spanning the distance from the cell surface to the viral glycoprotein.

Another advantage in using a second PEG chain (PEG4) linked to cholesterol (as cholesteryl-PEG4-NHS) for conjugation to the peptide trimer is that off-target conjugation is reduced. Attempts to directly conjugate cholesterol to the peptide trimer resulted in off-target conjugation. Conjugation of cholesteryl chloroformate to a PEG4 chain to generate cholesteryl-PEG4-COOH, which is then activated with NHS to form cholesteryl-PEG4-NHS, resulted in high conjugation specificity for primary amine groups, of which there is only one in the PIE12-2 trimer at the terminus of the PEG28 chain).

Further advantages are provided by conjugating peptides to the multimer scaffold prior to addition of cholesterol. Attempts to develop cholesteryl-PEG28-triNHS (scaffold with the cholesteryl conjugated on the terminal end of the PEG28 chain, to which peptides would be added) were problematic. Cholesterol-PEG28-triacid was successfully synthesized, however, activating the acids was difficult and peptides would not conjugate to this. Without wishing to be bound by theory, the product may have formed micelles that hid the acids from activation, and the peptides would not couple well, as the solvents that reduced micelle formation were incompatible with peptide solubility.

The fourth change is the composition of the pharmacokinetic enhancing cargo molecule. CPT24 utilizes a thiocholesterol moiety conjugated to the amino terminus of the PEG24 via a maleimide ester. Maleimide esters are problematic due to the ability of the thiocholesterol to react at either C3 or C4 of the maleimide ring, creating stereoisomers that are very difficult to separate. Furthermore, maleimide esters can undergo a base-dependent ring opening to yield a linear 5-carbon chain. CPT31 utilizes a cholesteryl chloroformate precursor that reacts with the terminal amino group of the fourth arm PEG chain to yield a cholesteryl carbamate linkage. This linkage does not create a stereocenter, and does not undergo degradation to yield an undesired by-product.

CTP31's low-mid pM potency, 18 h subcutaneous half-life, low clearance rate, and excellent bioavailability in non-human primates make CPT31 a very promising drug candidate for the treatment and/or prevention of HIV-1. The ultimate goal for CPT31 is to achieve monthly subcutaneous dosing when paired with a suitable subcutaneous extended-release depot such as GSK744 LA from GalaxoSmithKline (http://www.ncbi.nlm.nih.gov/pubmed/25589631) and rilpivirine (TMC278) (http://www.ncbi.nlm.nih.gov/pubmed/20160045) from Tibotec/Janssen Sciences. Given CPT31's extreme potency and PK properties, it is estimated that drug levels could be maintained at a strong therapeutic level (4 times the human serum-adjusted $IC_{90}$ in PBMCs) for 1 month in a 70 kg human given a ~40 mg monthly dose, which is well within reach given current depot-formulation technology.

Example 2

Additional Synthesis Methods for CPT31

Synthesis of FMOC-PEG28-triNHS

The following description outlines the synthesis of FMOC-PEG28-triNHS using FMOC-PEG28-COOH or BOC-PEG28-NHS and aminotriester (see also, FIG. 6, steps (1)-(3)).

(1) To conjugate FMOC-PEG28-COOH to an aminotriester scaffold, FMOC-PEG28-COOH was dissolved in a suitable polar organic solvent (e.g., dimethylformamide, dimethylacetamide, acetonitrile, or acetone) to a concentration of 200 mM. To this, one equivalent of (1-[Bis(methylamino)methylene]-1H-1,2,3-triazolo[4,5-b]pyridinium 3-oxid hexafluorophosphate) (HATU) was added, and the reaction was stirred for 5 minutes. One equivalent of N,N-diisopropylethylamine (DIPEA, Hunigs base) was then added, and the reaction was stirred for an additional 10 minutes. 2 equivalents of aminotriester were then added, and the reaction proceeded for 2 hours at room temperature. The resulting crude mixture was purified by reversed phase flash chromatography (C18 stationary phase) using a gradient of acetonitrile in water to yield the final product, tert-butyl 4-(3-{2-[2-(2-{2-[2-(2-{2-[2-(2-{2-[2-(2-{2-[2-(2-{2-[2-(2-{2-[2-(2-{2-[2-(2-{2-[(9H-fluoren-9-yl)methoxycarbonylamino]ethoxy}ethoxy)ethoxy]ethoxy}ethoxy) ethoxy]ethoxy}ethoxy)ethoxy]ethoxy}ethoxy)ethoxy] ethoxy}ethoxy)ethoxy]ethoxy}ethoxy)ethoxy] ethoxy}ethoxy)ethoxy]ethoxy}propionylamino)-4-(2-tert-butoxycarbonylethyl)heptanedioate (FMOC-PEG28-triester).

An alternative method to conjugate FMOC-PEG28-COOH (or BOC-PEG28-COOH) to the aminotriester multimer scaffold, 2 grams FMOC-PEG28-COOH (1.29 mmol) were added to a 50 ml round bottom flask equipped with a stir bar. 5 ml dry methylene chloride was then added to dissolve the PEG to a concentration of 250 mM. To this, 665 mg aminotriester was added (1.6 mmol, 1.25× acid), 175.6 mg 1-Hydroxy-7-azabenzotriazole (HOAt) (1.29 mmol, 1× acid). Once components were fully dissolved, the reaction was cooled to 0° C. in an ice bath, which helps to prevent the formation of the dead end o-acyl urea. 293 mg dicyclohexylcarbodiimide (DCC) (1.42 mmol, 1.1× acid) was dissolved in 500 μl DCM and was then added dropwise, and the reaction was run for 30 minutes at 0° C. before being removed from the ice bath and allowed to warm to room temperature. The reaction was complete by 150 minutes, at which time it was filtered to remove insoluble urea byproduct. Resulting crude reaction was then purified by flash chromatography using a gradient of ethanol in DCM (0-30%) using a 80 gram Biotage ZIP KP-SIL column with UV monitoring at 210 and 280 nm. Product was collected and dried by rotary evaporation to yield 1.8 grams of FMOC-PEG28-triNHS ester product (71% Yield).

Alternatively, N,N'-Dicyclohexylcarbodiimide (DCC) with catalytic amounts of 4-Dimethylaminopyridine (DMAP) or TEA may be used for conjugation of FMOC-PEG28-COOH to the aminotriester. However, this reaction was not nearly as efficient as DCC/HOAt in DCM. A potential risk when using DMAP is that it is more effective at removing the FMOC protecting group than trimethylamine (Et3N). The reaction appears to be near completion at 2-3 hours, but may be run longer to try and further increase yield.

In yet another alternative method, addition of N-hydroxysuccinimide (HOSu) (~1.1 equivalents) may be added to improve yield by creating the more stable ester intermediate. HOSu solubility in DCM is fairly poor, so dimethylformamide (DMF) or DMAc may be added dropwise until HOSu is in solution, which is around 5-10% of the reaction volume. However, reaction yield was not improved with HOSu and a significant amount of FMOC-PEG28-COOH was lost (20-30%) as the FMOC-PEG28-triester forms but fails to react efficiently.

A variety of columns (e.g., Biotage SNAP ultra column, Biotage ZIP column) may be used for purification of FMOC-PEG28-triester reaction product. The FMOC group makes purification simple due to very strong absorbance at 215 nm. Residual DMF or DMAc can complicate the purification due to strong absorbance in the same region. Flash purification at 0% ethanol to remove residual DMF or DMAc may be performed before starting the ramp to 30% ethanol. Also, a higher wavelength could be used (300 nM) to avoid the interference from DMF. Both the FMOC-PEG28-COOH and FMOC-PEG28-triester elute around 5-6% ethanol.

If BOC-PEG28-COOH is used for the fourth arm on the multimer scaffold, improved coupling may occur, as a larger amount of base may be used without concern of removing the FMOC group. However, an evaporative light scattering detector may be needed for detection of non-volatile compounds, as without FMOC there is no chromophore to follow.

Other coupling reagents such as Diisopropylcarbodiimide (DIC) and HATU, may be used for this step and permit HPLC purification directly from the reaction. However, these coupling reagents resulted in lower yields than when DCC was used.

(2) Next the FMOC-PEG28-triester underwent deprotection of the triester (see, Step (2) of FIG. 6). Purified FMOC-PEG28-triester was dissolved in DCM (20% solution) and placed in an ice bath to cool. Once cool, 25 equivalents TFA per acid group (75 equivalents total) was added dropwise while stirring. After 30 min, the reaction was allowed to warm to room temperature, and the reaction was continued for 60 min. The reaction was then dried by rotary evaporator to remove DCM and TFA prior to being resuspended in 20% Acetonitrile. This solution was then purified using a reverse phase flash cartridge on a Biotage Isolera™ flash purification system using a water/acetonitrile gradient with 0.1% TFA. The correct product (with all three tert groups removed) elutes earliest in the gradient. In instances where deprotection is incomplete, the −1 and −2 t-butyl material elutes between the correct product and the starting material. Resulting product was dried by rotary evaporation, which may be followed by repeated azeotropic distillations from toluene to remove residual water after extensive rotary evaporation time. Alternative drying methods includes recrystallization or lyophilization. 100% yield of FMOC-PEG28-triacid was obtained.

FMOC-PEG28-triacid can also be purified by flash chromatography with using the same gradient described above (a gradient of ethanol in DCM). However, it is critical to dry the product extensively, as the presence of ethanol in subsequent steps is severe consequences, with a substantial propensity towards transesterification of the three acids. Other more volatile polar solvents to elute the FMOC-PEG28-triacid were also tested for reduction of the potential for transesterification, but due to the strong polar nature of the molecule with three acids and a long PEG chain, ethanol or methanol is preferred. It may be possible to reduce this complexity with improved flash solvent systems, however, due to the severe losses in yield, reverse phase flash cartridges are preferred.

(3) The FMOC-PEG28-triacid was activated using N'N'-Disuccinimidyl carbonate 1.8 grams FMOC-PEG27-aminotriacid (1.014 mmol), 909 mg N'N'-disuccinimidyl carbonate (3.55 mmol, 1.15× each acid) and 750 µmol Et3N were added to 12 ml dry acetonitrile (see also, FIG. 6, step (3)). The reaction was stirred for 90 minutes before purification by flash chromatography (0-10% Methanol gradient in DCM, product followed by 215 signal from FMOC group). Product was immediately dried down by rotary evaporation to yield a clear glassy product totaling 2.2 grams (85% Yield).

This method was adapted from Ogura et al. (Tetrahedron Letters, 1979, 49: 4745-4746). Ogura et al. calls for a 1:1:1 molar ratio of carboxylic acid:DSC:pyridine, but this is not suitable for activating FMOC-PEG28-triacid as the pyridine will very rapidly remove the FMOC group. However, in other instances where triacids without an FMOC group are activated, the protocol as described in Ogura et al. may be used. If a base stable protecting group such as BOC is used instead of FMOC, it is preferred to use pyridine at an equimolar ratio instead of the 0.2× Et3N as described above. Alternatively, HOSu may be used as an activating agent.

Conjugation of PIE12-2 Peptides to the Multimer Scaffold

The conjugation of PIE12 to the activated scaffold from step (3) of FIG. 6 was carried out through the reaction of the NHS ester on the scaffold (1 NHS per scaffold arm, with 3 arms per molecule) to the unique primary amine of PIE12-2 located on the side chain of the C-terminal lysine (see also, FIG. 6, step (4)). This is the only free amine on the peptide.

This reaction was carried out in dry polar organic solvent, dimethylacetamide, in the presence of the tertiary base trimethylamine (Et3N) under an inert gas atmosphere. PIE12-2 peptide was used in the reaction at a 3.3:1 molar ratio to the scaffold, or a 1.1:1 molar ratio to each NHS ester (since each trimer molecule has 3 arms, and 3 NHS esters, the final ratio is 3.3:1). In the final reaction solution, the PIE12-2 peptide concentration was 10 mM, the scaffold concentration was 3.03 mM, and the Et3N concentration was 150 mM.

To set up the reaction, a solution stock of scaffold at a suitable concentration in DMAc (usually 250 mM) was made immediately prior to initiating the peptide conjugation reaction. PIE12-2 peptide was dissolved in DMAc to a concentration of 12 mM and required TEA was added to achieve 150 mM in the final volume. Scaffold was added to the reaction, then any additional DMAc was added to achieve the final reaction concentrations.

Figure 7:
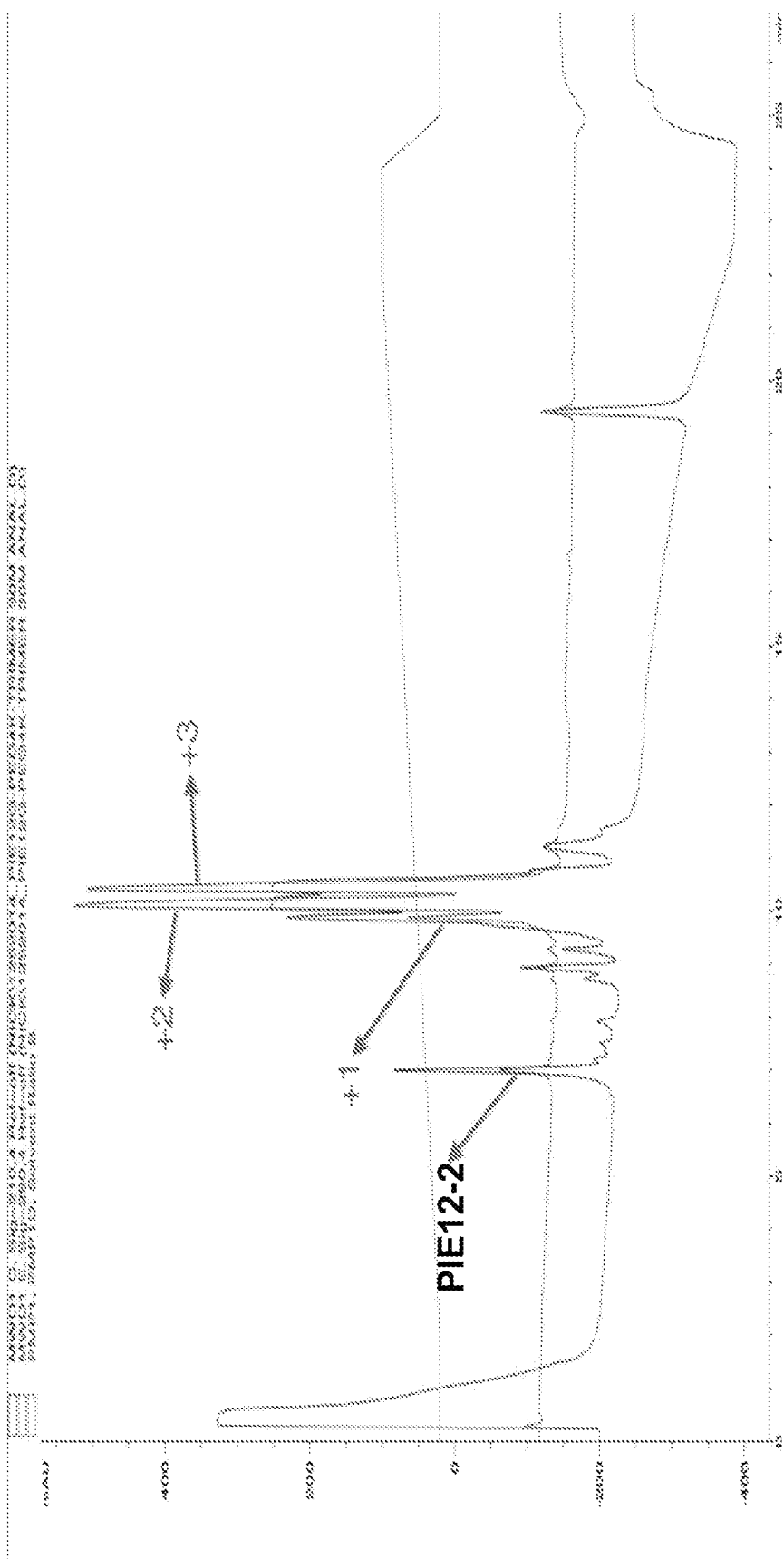
FIG. 7 depicts an HPLC analytical trace showing the reaction at step 4 of FIG. 6 of CPT31 synthesis. A peak representing the PIE12-2 monomer, and peaks representing the addition of 1, 2, and 3 PIE12-2 peptides to the FMOC-PEG$_{28}$-triNHS scaffold (+1, +2, +3 peaks, respectively) are shown. Trace was intentionally run at sub-optimal conditions to illustrate all possible products. When using high quality scaffold and run at optimal conditions, yields are significantly improved.

The reaction was maintained at room temperature for 120 minutes. Reaction progress was verified by HPLC. The HPLC trace of FIG. 7 shows the starting material, as well as three peaks that represent the addition of 1, 2 and 3 PIE12-2 peptides (this reaction was run at suboptimal conditions to illustrate the three species). The peak for +3 peptides represents the desired product. With a highly active NHS ester scaffold, there will be very little (often none) of the +1 product, and much less of the +2 product. In view of this, it is preferred that conjugation of the peptides to the scaffold be carried out in very high quality dry solvents and under a dry inert gas. Amine contamination competes with the PIE12-2 peptide and reduces yields. Water hydrolyzes the NHS ester and also reduces yields. When DMF was used as the reaction solvent, it was found that even high quality DMF had more amine contamination that DMAc, and over time DMF broke down to form a free amine.

The reaction yield is highly dependent upon the state of the FMOC-PEG28-triNHS scaffold. With a highly active scaffold (e.g., all three arms are NHS activated), yields are ~75%. This value refers to the amount of peptide compared to peptide mass incorporated into the scaffold. Since the PIE12-2 peptide was used in excess of the scaffold, the yields were never going to exceed 85% if the reaction was followed as described herein. PIE12-2 dimers are almost always present in small levels, but the amount can be decreased by using high quality dry solvents and freshly prepared and high quality scaffold.

Figure 8:
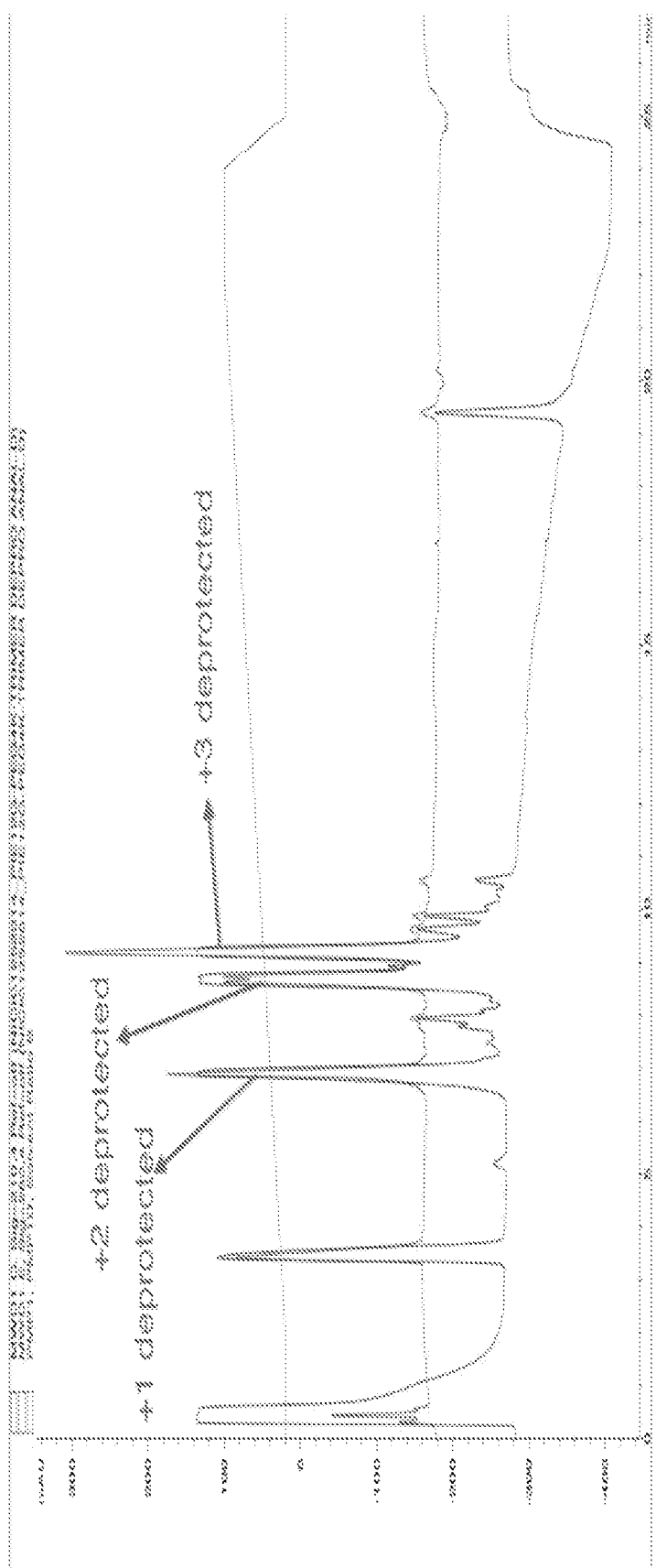
FIG. 8 depicts HPLC analytical trace showing the reaction at step 5 of FIG. 6 of the synthesis of CPT31. The same peaks as in FIG. 7 are shown after removal of the FMOC protecting group from FMOC-PEG28-PIE12-2 trimer using piperdine to yield NH2-PEG28-PIE12-2 trimer. Trace was intentionally run at sub-optimal conditions to illustrate all possible products. When using high quality scaffold and run at optimal conditions, yields are significantly improved.
Figure 9:
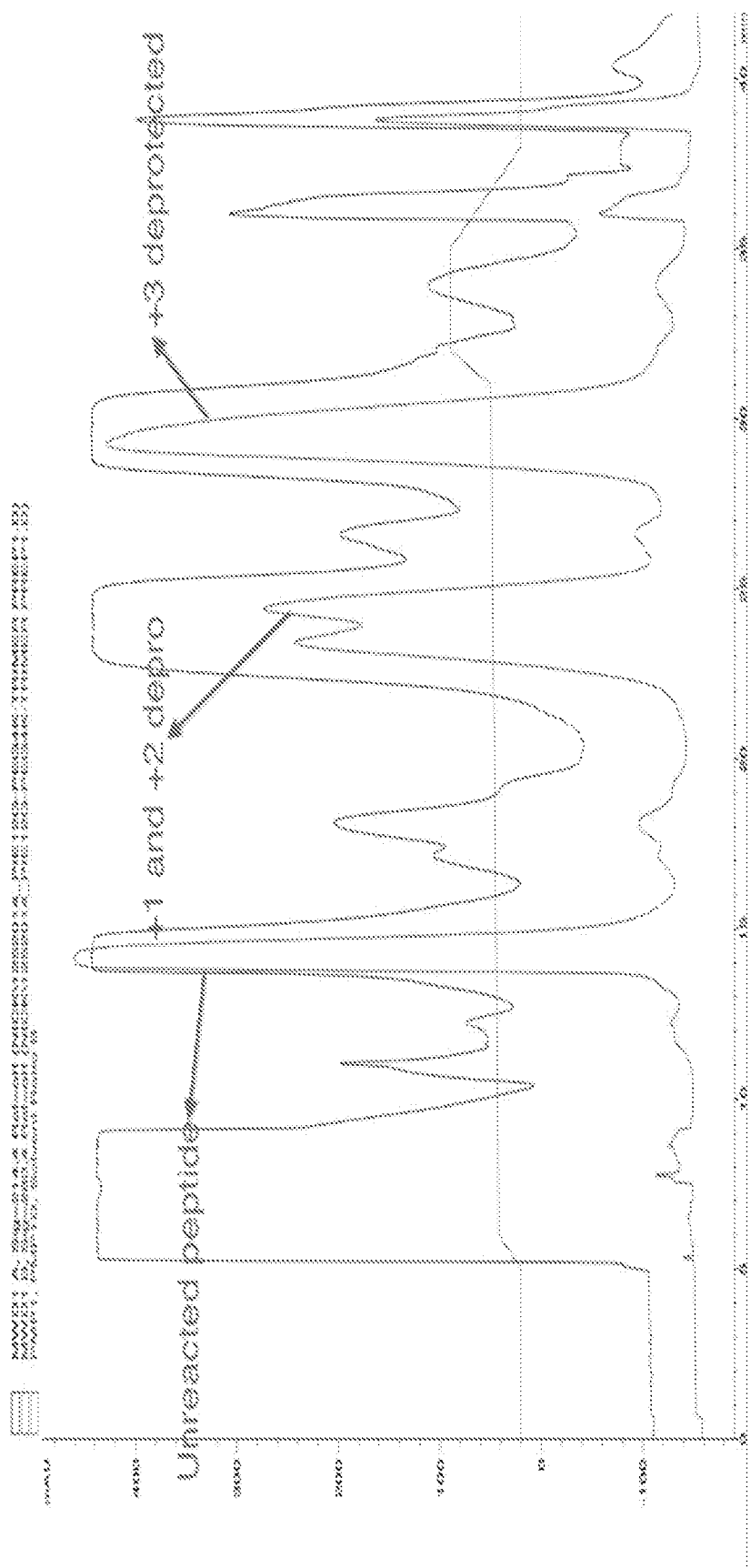
FIG. 9 depicts HPLC preparation trace of the reaction at step 5 of FIG. 6 of the synthesis of CPT31. Trace was intentionally run at sub-optimal conditions to illustrate all possible products. When using high quality scaffold and run at optimal conditions, yields are significantly improved.

Once the conjugation reaction has gone to completion (usually around 120 minutes), piperdine is added to the reaction to a final concentration of 25% to remove the FMOC protecting group (see also, FIG. 6, step (5)). This combination was allowed to react for 30 minutes before purification by HPLC (Waters)(Bridge Peptide BEH C18 column). This step is quantitative. An analytical HPLC trace of the deprotection reaction is shown in FIG. 8, and a preparative HPLC trace of the deprotection reaction is shown in FIG. 9. Preferably, the deprotected trimer is purified by HPLC from the crude reaction mixture. This reaction step may be the most critical step in the synthesis of CPT31 and the most susceptible to severe losses. Attempts to purify the trimer (after FMOC deprotection) using precipitation into MTBE resulted in precipitation of all components, and no purification is achieved. Moreover, precipitation from DMAC into MTBE at a relatively small ratio resulted in a loss of a substantial amount of material, which was soluble in the DMAC/MTBE solution.

Solid Phase Synthesis of Cholesteryl-PEG4-NHS

Cholesteryl-PEG4-NHS is coupled to the NH2-PEG28-PIE12-2 trimer in the final conjugation step. Attempts to develop cholesteryl-PEG28-triNHS (scaffold with the cholesteryl conjugated on the terminal end of the PEG28 chain, to which peptides would be added) were problematic. Cholesterol-PEG28-triacid was successfully synthesized, however, activating the acids was difficult and peptides would not conjugate to this. Without wishing to be bound by theory, the product may have formed micelles that hid the acids from activation, and the peptides would not couple well, as the solvents that reduced micelle formation were incompatible with peptide solubility.

Thus, a synthesis method was developed, where the peptide is coupled to the multimer scaffold prior to cholesterol addition. This approach was also beneficial for another reason. Once cholesterol is added, it is very difficult to discriminate by HPLC purification a multimer scaffold that has the appropriate three PIE12-2 monomers attached thereto from a multimer scaffold with one and two PIE12-2 peptides attached.

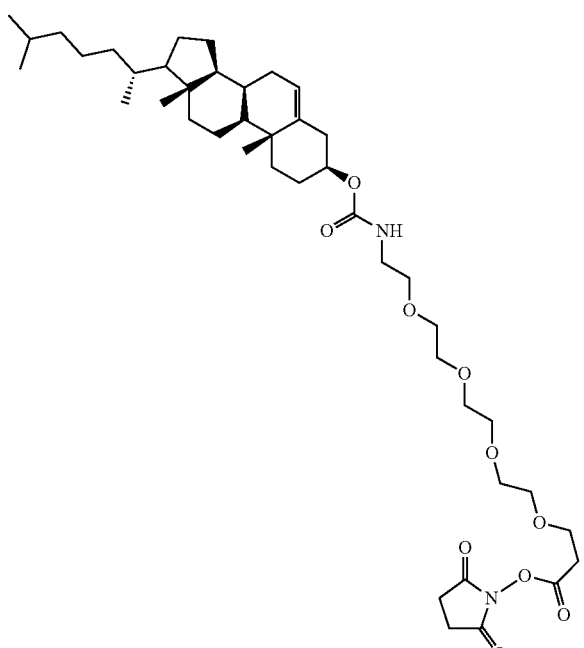

Cholesteryl-PEG4-NHS
774.5029 Da (monoisotopic mass)
$C_{43}H_{70}N_2O_{10}$

The synthesis of cholesteryl-PEG4-NHS molecule (above) is carried out using a solid support (e.g., 2-Chlorotrityl chloride resin, a very acid labile resin), which makes the work-up much easier. Preferably, a standard resin is not utilized, as the cleavage conditions in harsh acid promote modification of the cholesterol (primarily through addition across the double bond in ring 2 of cholesterol, though other modifications are possible).

An exemplary synthesis reaction is summarized as follows. 22.12 grams of 2-chlorotrityl chloride resin (22.56 mmol active sites, 1.1× acid) was swelled in dry dichloromethane (DCM) for 30 minutes, then washed 3× with DCM. To this was added 10 grams of FMOC-PEG4-COOH (20.51 mmol) in 60 ml DCM with 17.86 ml DIPEA (5× acid). The reaction was clearly evident by the evolution of gas. Reaction was allowed to proceed for 90 minutes with agitation (nitrogen bubbling through RV). Resin was washed 5× with DCM. Remaining active sites were capped by the addition of 100 ml DCM:MeOH:DIPEA (17:2:1) with gas agitation for 60 min. Resin was washed 5× with DCM.

The FMOC group was then deprotected by adding 100 ml DMF:DCM:Piperdine (1:1:1) with mixing for 30 minutes. Resin was then washed 3× with 1:1 DMF:DCM, then 2× with DCM. Cholesteryl chloroformate was then added (18 grams, 41.02 mmol, 2× amine) in 60 ml DCM with DIPEA (41.02 mmol, 1× cholesteryl chloroformate). This combination was reacted for 60 min with gas agitation, then washed 5× with DCM.

Product was cleaved from resin using 100 ml of 5% TFA in DCM for 2 hours. Cleavage cocktail was collected, and resin was rinsed with 20 ml DCM, which was combined with cleavage cocktail. The eluent was partially dried with rotary evaporation before purification by flash chromatography using a 120 g Biotage ZIP column on a Biotage Isolera™ flash purification system (0-50% gradient of isopropyl alcohol (IPA) in hexane) with monitoring at 254 nM.

Product was extensively dried by rotary evaporation to yield a viscous, yellowish oil totaling 9.6 grams, 65% yield.

This product was then resuspended in dry acetonitrile and warmed to 40° C. To this was added N'N-Disuccinimidyl carbonate (1.1× acid) and triethylamine (2×DSC). This reaction was stirred at 40° C. for 60 min (again, reaction was evident by the evolution of gas) prior to purification by flash chromatography (0-100% ethanol in DCM) with monitoring at 254 nm. Product was dried down extensively by rotary evaporation to yield the final product, Cholesteryl-PEG4-NHS in 90% yield.

Liquid Phase Synthesis of Cholesteryl-PEG4-NHS

As an alternative to the solid phase synthesis, a solution phase synthesis method of cholesteryl-$PEG_4$-COOH was utilized. $NH_2$-$PEG_4$-COOH was dissolved in methylene chloride to a concentration of 0.5 M. 1 equivalent of cholesteryl chloroformate was added, and the solution was stirred until the cholesteryl chloroformate was completely dissolved. 0.6 equivalents of N,N-diisoppropylethlamine (DIPEA) was then added, and the reaction was stirred under atmosphere at room temperature for 4 hours. The reaction was quenched by the addition of 0.6 equivalents of acetic acid, and the crude product was dried by rotary evaporation, then purified by flash chromatography using a gradient of isopropanol in methylene chloride to yield the pure final product, Cholesteryl-$PEG_4$-COOH in 90% yield as a viscous amber oil.

The mass of this product was verified by mass spectrometry, and compared by LC/MS to the solid-phase produced cholesteryl-$PEG_4$-COOH.

The solution phase approach described herein provided a substantial improvement on the solid-phase synthetic route. Yield was significantly increased, and the solution phase approach did not require the use of significant excesses of Cholesteryl chloroformate, an expensive reagent. Moreover, by eliminating the solid phase support, the reaction cost was reduced and variability in the reaction was eliminated. Finally, by eliminating the solid phase support, the need for exposing the labile cholesterol to TFA (a strong organic acid) was eliminated, thus avoiding the potential for modification of the cholesterol group (such as oxidation).

Cholesterol Addition to PEG28-PIE12-2 Trimer

Figure 10:
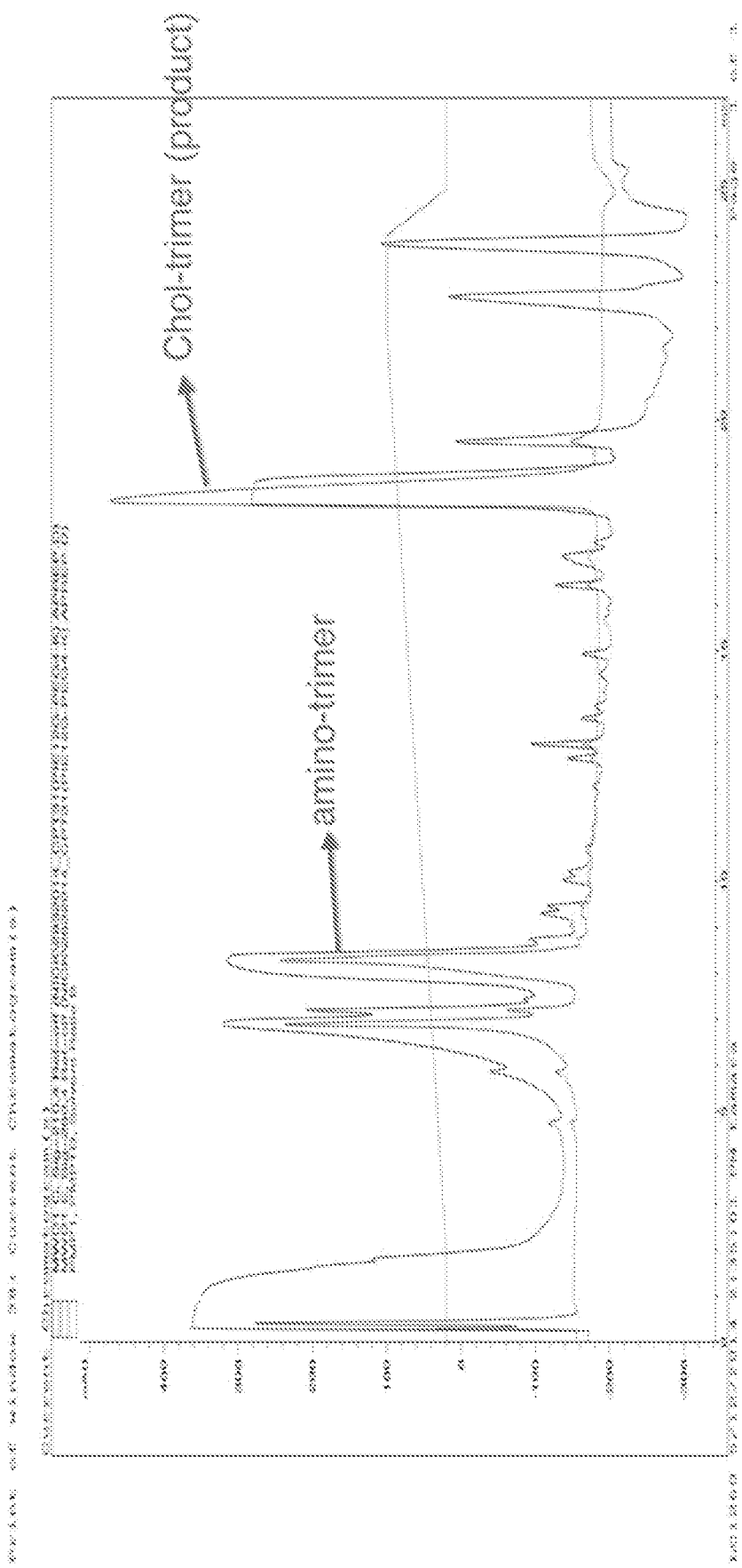
FIG. 10 depicts HPLC analytical trace showing addition of the cholesterol moiety to the free amino at the terminal end of the PEG$_{28}$ of the multimer scaffold (step 6 of FIG. 6). Trace was intentionally run at sub-optimal conditions to illustrate all possible products. When using high quality scaffold and run at optimal conditions, yields are significantly improved.

The final step in the synthesis of CPT31 is the addition of cholesterol to the terminal amine of the PEG28 chain of the fourth arm of the NH2-PEG28-PIE12-2 trimer, mediated by reaction of the NHS ester of cholesteryl-PEG4-NHS and the PEG amine of the fourth arm. Cholesteryl-PEG4-NHS contains an active NHS ester. Preferably, cholesteryl-PEG4-NHS is stored in container at −20° C. until the conjugation reaction is set up in order to preserve NHS activity. Allow cholesteryl-PEG4-NHS to warm to room temperature before use. Do not open container of cholesteryl-PEG4-NHS prior to warming to room temperature to avoid condensation that can induce NHS loss. Once the cholesteryl-PEG4-NHS is at room temperature, a stock solution of dry dimethylacetamide (DMAc) was prepared. The reaction was carried out in high grade DMAc in the presence of trimethylamine (preferably fresh). The reaction is highly sensitive to water. For this reason, high grade DMAc and fresh trimethylamine are used. Older trimethylamine can form primary and secondary amines, which can compete with the peptide for conjugation to the NHS ester group. Preferably, 24 hours prior to use, add molecular sieves to further reduce water content in DMAc. Preferably, dimethylformamide is not used as the solvent unless it is extremely dry and freshly prepared. Dimethylformamide has a tendency to break down and form primary and secondary amines, which may dramatically reduce the efficiency of the reaction. Reaction set-up is similar to above, with peptide trimer being first dissolved in DMAc to a concentration above 10 mM (10 mM-100 mM), then triethylamine is added, followed by the Cholesteryl-PEG4-NHS (1.1-2 equivalents), then the volume is adjusted so that the trimer is at 10 mM. The reaction is carried out at room temperature with stirring/agitation for 2-3 hours before purification by HPLC. The final product sticks to glass, potentially causing severe losses. Preferably, the final product is collected in plastic and all downstream steps are performed in plastic (e.g., lyophilization). The shift upon cholesterol addition is dramatic, as illustrated in the trace below. Yield for this step when reaction conditions are correct (e.g., an excess of the cholesteryl-PEG-NHS) are nearly quantitative. The HPLC trace set forth in FIG. 10 depicts an intentionally lower yield to illustrate the peak shift upon conjugation. Preferably, the coupling the purification reaction is completed in a single day.

Synthesis of FMOC-PEG28-triPFP

To evaluate the use of the more stable pentafluorophenyl (PFP) ester as the functional group used in the synthesis of CPT31 instead of NHS ester, FMOC-PEG28-triPFP was synthesized and evaluated for stability in standard CPT31 reaction conditions.

FMOC-PEG28-triPFP was synthesized essentially as described for the synthesis of FMOC-PEG28-triNHS. Briefly, FMOC-PEG28-triacid was dissolved in a suitable volume of acetonitrile heated to 40° C. with stirring. Once fully dissolved, 4 equivalents (relative to FMOC-PEG28-triacid) of PFP carbonate were added, followed by 1 equivalent of trimethylamine (relative to FMOC-PEG28-triacid). The reaction was carried out under atmosphere at 40° C. with regular analysis to determine completeness of activation. During the course of the reaction an additional 4 equivalents were added to achieve sufficient activation of the scaffold for further evaluation (yield was ~40%)

Once the reaction was complete, the product was purified by flash chromatography using a gradient of ethanol in methylene chloride, and the resulting product was dried by rotary evaporation to yield a viscous, straw colored oil.

To evaluate the potential for improved yields during peptide coupling that may be afforded by the use of the more stable PFP ester, a standard peptide coupling reaction was set up. 3.3 equivalents of PIE12-2 (relative to scaffold) were dissolved in dimethylacetamide to a concentration of 10 mM. To this was added trimethylamine to a final concentration of 150 mM. Finally, FMOC-PEG28-triPFP scaffold was dissolved in a minimal volume of dimethylacetamide and added to the reaction. The reaction was examined by HPLC at regular intervals until no further progress was observed (24 hours), and the resulting yield was quantified by integrating peak areas of reaction products using UV absorbance.

FMOC-PEG28-triacid was successfully activated using PFP carbonate to yield FMOC-PEG28-triPFP. The yield of the peptide coupling reaction between FMOC-PEG28-triPFP showed approximately 50% conversion to the desired FMOC-PEG28-(PIE12-2)$_3$ after 24 hours.

For comparison, the FMOC-PEG28-triNHS reaction achieves ~80% conversion to FMOC-PEG28-PIE12$_3$ in three hours, a substantially improved yield when compared to PFP ester.

Furthermore, activation of the FMOC-PEG28-triacid scaffold with PFP esters is more difficult. To achieve similar activation of the triacid scaffold, twice the amount of ester-carbonate was required when PFP carbonate is used. This may be due to the increased size of the PFP ester, leading to steric hindrance at the activation site.

Given that PFP carbonate is approximately 20× more expensive than disuccinimidyl carbonate, and at least twice the amount is required for activation of the scaffold, PFP ester presents a substantial increase in cost for the synthesis of the ester activated scaffold.

Another observation is that the reaction rate of the PFP ester is significantly slower than that of NHS ester. This requires much longer reaction times for CPT31 synthesis, and as a result, the peptide is exposed to organic solvent and base for a much greater period of time. Such exposure increases the risk of peptide modification that could be inseparable by standard purification approaches. For these reasons, NHS ester is the synthetic route to be used in the synthesis of CPT31, unless reaction yields are improved and costs are decreased in the future.

Though PFP esters provide greater stability than the related NHS esters, synthesis of CPT31 is preferably carried out using NHS esters, unless reaction yields associated with PFP esters improve and costs decrease. NHS ester activation is significantly less costly than PFP ester activation, NHS ester has a faster reaction rate than PFP ester, and NHS esters provide greater yield of the FMOC-PEG28-(PIE12-2)$_3$.

All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/276,201 and U.S. Provisional Patent Application No. 62/372,257, are incorporated herein by reference, in their entirety.

The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising at least one PIE12-2 D-peptide comprising SEQ ID NO:3 [Ac-HPCDYPEWQWL-CELG-(PEG$_4$)-K—NH$_2$], wherein the at least one PIE12-2 D-peptide interacts with the N-trimer pocket of HIV gp41.

2. The composition of claim 1, comprising at least two PIE12-2 D-peptides comprising SEQ ID NO:3 [Ac-HP-CDYPEWQWLCELG-(PEG$_4$)-K—NH$_2$].

3. The composition of claim 1, comprising at least three PIE12-2 D-peptides comprising SEQ ID NO:3 [Ac-HP-CDYPEWQWLCELG-(PEG$_4$)-K—NH$_2$].

4. The composition of claim 3 comprising three PIE12-2 D-peptides, wherein each PIE12-2 D-peptide is linked to an arm of a multimer scaffold comprising three arms via an amide bond between the epsilon amino group of the C-terminal D-lysine of the PIE12-2 D-peptide and a carboxyl group of the arm of the multimer scaffold, wherein the multimer scaffold is based on 4-Amino-4-(2-carboxyethyl) heptanedioic acid.

5. The composition of claim 4, wherein each PIE12-2 D-peptide and linkage to the multimer scaffold is as shown in FIG. 4B.

6. The composition of claim 4, wherein the multimer scaffold further comprises a fourth arm linking a cholesterol moiety via a polyethylene glycol (PEG) linker to the multimer scaffold, wherein the total number of ethylene glycol repeats in the fourth arm ranges from 12-132, and optionally wherein the cholesterol moiety is linked to the PEG linker via a carbamate linkage.

7. The composition of claim 6, wherein the PEG linker comprises a first PEG chain and a second PEG chain linked in series linking the cholesterol moiety to the multimer scaffold.

8. The composition of claim 7, wherein the total number of ethylene glycol repeats in the fourth arm is 32 and the first PEG chain comprises 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 ethylene glycol repeats and the second PEG chain comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 ethylene glycol repeats, respectively.

9. The composition of claim 6, wherein the PEG linker is linked to the multimer scaffold via an amide bond.

10. The composition of claim 7, wherein the second PEG chain is linked to the first PEG chain via an amide bond.

11. The composition of claim 6, wherein the cholesterol moiety is cholesteryl chloroformate.

12. The composition of claim 7, wherein the first PEG chain is linked to the multimer scaffold prior to linking of the cholesterol moiety and second PEG chain, and the composition is optionally purified prior to linking of the cholesterol moiety and second PEG chain.

13. The composition of claim 6, wherein addition of the cholesterol moiety to the fourth arm does not create stereoisomers.

14. The composition of claim 7, wherein the cholesterol moiety is attached to the fourth arm of the multimer scaffold via the second PEG chain and is cholesteryl-PEG4-NHS ester as shown in the following figure:

15. The composition of claim 6, comprising at least one trimeric PIE12-2 D-peptide-cholesterol conjugate having the following structure:

16. A pharmaceutical composition comprising a composition of claim 1 and a pharmaceutically acceptable carrier.

17. The composition of claim 1, further comprising at least one anti-viral agent selected from a viral replication inhibitor, a viral protease inhibitor, a viral reverse transcriptase inhibitor, a viral entry inhibitor, a viral integrase inhibitor, a viral Rev inhibitor, a viral Tat inhibitor, a viral Nef inhibitor, a viral Vpr inhibitor, a viral Vpu inhibitor, and a viral Vif inhibitor.

18. A method of inhibiting HIV entry into a host cell comprising exposing the virus to a composition of claim 1, thereby inhibiting HIV entry into the host cell.

19. A method of treating HIV infection in a subject comprising administering to the subject an effective amount of a composition of claim 1, thereby treating HIV infection.

20. A method of synthesizing a trimeric D-peptide-cholesterol conjugate of the following structure,

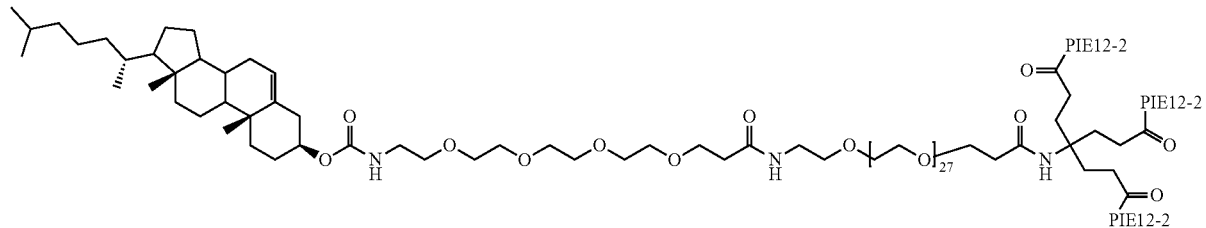

wherein the method comprises the steps as set forth in FIG. 6.

21. The pharmaceutical composition of claim 16, wherein the pharmaceutical composition is a depot formulation.

* * * * *